US012721823B2

(12) United States Patent
Martynyuk et al.

(10) Patent No.: US 12,721,823 B2
(45) Date of Patent: Sep. 1, 2026

(54) METHODS AND COMPOSITIONS FOR TREATMENT OF LOW CIRCULATING TESTOSTERONE CONDITIONS

(71) Applicant: University of Florida Research Foundation, Inc., Gainesville, FL (US)

(72) Inventors: Anatoly Eugeny Martynyuk, Gainesville, FL (US); Lingsha Ju, Gainesville, FL (US); Timothy E. Morey, Gainesville, FL (US); Nikolaus Gravenstein, Gainesville, FL (US); Christoph N. Seubert, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 443 days.

(21) Appl. No.: 18/549,288

(22) PCT Filed: Mar. 25, 2022

(86) PCT No.: PCT/US2022/021852
§ 371 (c)(1),
(2) Date: Sep. 6, 2023

(87) PCT Pub. No.: WO2022/204459
PCT Pub. Date: Sep. 29, 2022

(65) Prior Publication Data

US 2024/0165049 A1 May 23, 2024

Related U.S. Application Data

(60) Provisional application No. 63/166,043, filed on Mar. 25, 2021.

(51) Int. Cl.
*A61K 31/08* (2006.01)
*A61P 15/08* (2006.01)

(52) U.S. Cl.
CPC .............. *A61K 31/08* (2013.01); *A61P 15/08* (2018.01)

(58) Field of Classification Search
CPC ................................ A61K 31/08; A61P 15/08
See application file for complete search history.

(56) References Cited

U.S. PATENT DOCUMENTS

2018/0116997 A1* 5/2018 Brosnan .................. A61P 43/00

FOREIGN PATENT DOCUMENTS

KR 10-2016-0118844 * 10/2016 ........... A61K 36/815
KR 10-2016-011884 A 12/2016

OTHER PUBLICATIONS

Bevinaguddaiah, et al, Prader-Willi syndrome with Oculocutaneous Albinism: Anesthetic Implications and Management, Nat. J. Lab. Med., vol. 3(2), pp. 13-15 (2014). (Year: 2014).*
Macksey, et al, Anesthetic Management in a Pediatric Patient with Noonan Syndrome, Mastocytosis, and von Willebrand Disease: A case report, AANA J., vol. 75, No. 4, pp. 261-264 (2007). (Year: 2007).*
Ju, et al., Intergenerational Effects of Sevoflurane in Young Adult Rats, Anesthesiology, vol. 131, No. 5, pp. 1092-1109 (Nov. 2019). (Year: 2019).*
I'ntl Search Report and Written Opinion of PCT /US2022/021852 mailed on Jun. 22, 2022.
Bevinaguddaiah et al., Prader-Willi syndrome with Oculocutaneous Albinism: Anaesthetic Implications and Management, National Journal of Laboratory Medicine, vol. 3, No. 2, Jun. 30, 2014, pp. 13-15.
Macksey et al., Anesthetic Management in a Pediatric Patient with Noonan Syndrome, Mastocytosis, and Von Willebrand Disease: A Case Resport, American Association of Nurse Anesthesiology Journal, Aug. 2007, vol. 75, No. 4, pp. 261-264.
Ju et al., Intergenerational Effects of Sevoflurane in Young Adult Rats, Anesthesiology, Nov. 2019, vol. 131, No. 5, pp. 1092-1109.

* cited by examiner

*Primary Examiner* — Erich A Leeser
(74) *Attorney, Agent, or Firm* — Thomas | Horstemeyer, LLP

(57) ABSTRACT

In one aspect, the disclosure relates to methods of treating a subject having a clinical condition associated with low circulating levels of testosterone, comprising: administering to the subject a therapeutically effective dose of sevoflurane, thereby treating the clinical condition associated with low circulating levels of testosterone. In some aspects, the sevoflurane can be administered nasally or by inhalation. In another aspect, exposure to sevoflurane results in long-term increase in serum levels of testosterone in the subject (e.g., 60 days to 120 days). This abstract is intended as a scanning tool for purposes of searching in the particular art and is not intended to be limiting of the present disclosure.

19 Claims, 11 Drawing Sheets

Specification includes a Sequence Listing.

SEQUENCE LISTING

```
<160> NUMBER OF SEQ ID NOS: 2

<210> SEQ ID NO 1
<211> LENGTH: 34
<212> TYPE: DNA
<213> ORGANISM: Artificial sequence
<220> FEATURE:
<223> OTHER INFORMATION: Synthetic construct

<400> SEQUENCE: 1

gattgtaagt gtttttatta ttgagttgta tatt                              34


<210> SEQ ID NO 2
<211> LENGTH: 25
<212> TYPE: DNA
<213> ORGANISM: Artificial sequence
<220> FEATURE:
<223> OTHER INFORMATION: Synthetic construct

<400> SEQUENCE: 2

aataaacttt tcccctttta taccc                                        25
```

METHODS AND COMPOSITIONS FOR TREATMENT OF LOW CIRCULATING TESTOSTERONE CONDITIONS

CROSS-REFERENCE TO RELATED APPLICATIONS

This application is the 35 U.S.C. § 371 national stage application of PCT application serial number PCT/US2022/021852, filed on Mar. 25, 2022, which claims priority to U.S. provisional application entitled "METHODS AND COMPOSITIONS FOR TREATMENT OF LOW CIRCULATING TESTOSTERONE CONDITIONS," having Ser. No. 63/166,043, filed on Mar. 25, 2021, which are entirely incorporated herein by reference.

STATEMENT REGARDING FEDERALLY SPONSORED RESEARCH OR DEVELOPMENT

This invention was made with government support under grant numbers R56 HD102898 and R01 HD107722, awarded by the National Institutes of Health. The government has certain rights in the invention.

BACKGROUND

Hypogonadism is defined as a state of low circulating testosterone with concurrent symptoms and impacts on physical and mental well-being. Symptomatology includes low libido, erectile dysfunction, poor energy, decreased lean muscle mass, increased body fat gain, impaired cognition, and depression. Additionally, androgen deficiency has been associated with negative consequences for cardiovascular health, metabolism, and longevity. Hypergonadotropic hypogonadism is a feature of certain genetic diseases (Klinefelter's Syndrome, Noonan Syndrome) as well as cases of testicular injury (torsion, trauma) or congenital anorchidism. Secondary hypogonadism, also known as hypogonadotropic hypogonadism, is defined as a failure in gonadotropin production in the central nervous system. Associated conditions include prolactinoma and other pituitary tumors, hemochromatosis, and other genetic disorders (Prader-Willi syndrome, Kallmann's syndrome). Of particular interest is late onset hypogonadism, as testosterone production decreases yearly after the age of 40 as a result of insidious changes in the testis or central nervous system, with variable consequences for clinical symptoms in men. The Massachusetts Male Aging Study and the Boston Area Community Health Survey substantiate the prevalence of symptomatic androgen deficiency increases with advancing age.

Over the last 2 decades, testosterone replacement therapy prescriptions have increased between 1.8- and 4-fold. After 1 yr, 80-85% of men discontinue testosterone replacement therapy [7-9]. The efforts continue to develop alternative means of testosterone replacement or augmenting endogenous testosterone production given the inherent burden to patients of transference and daily dosing with topicals, pain with injections, and invasiveness with pellet administration. The development of novel therapies remains an area of active investigation.

Despite advances in testosterone replacement therapy research, there is still a scarcity of compounds that are both potent, efficacious, and noninvasive and also effective in the treatment of low circulating testosterone and diseases in which low circulating testosterone is involved. These needs and other needs are satisfied by the present disclosure.

SUMMARY

In one aspect, the disclosure relates to methods of treating a subject having a clinical condition associated with low circulating levels of testosterone, comprising: administering to the subject a therapeutically effective dose of sevoflurane, thereby treating the clinical condition associated with low circulating levels of testosterone. In some aspects, the sevoflurane can be administered nasally or by inhalation. In another aspect, exposure to sevoflurane results in long-term increase in serum levels of testosterone in the subject (e.g., 60 days to 120 days).

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 11B shows that effects of SEVO and surgery (to induce traumatic brain injury, TBI) and TBI interact to induce even greater increases in testosterone levels. FIGS. 11C-11D shows that the combined effects of SEVO, surgery and TBI to induce increases in testosterone levels may not be explained by just their cummulative stress-like effects.

Figure 1:
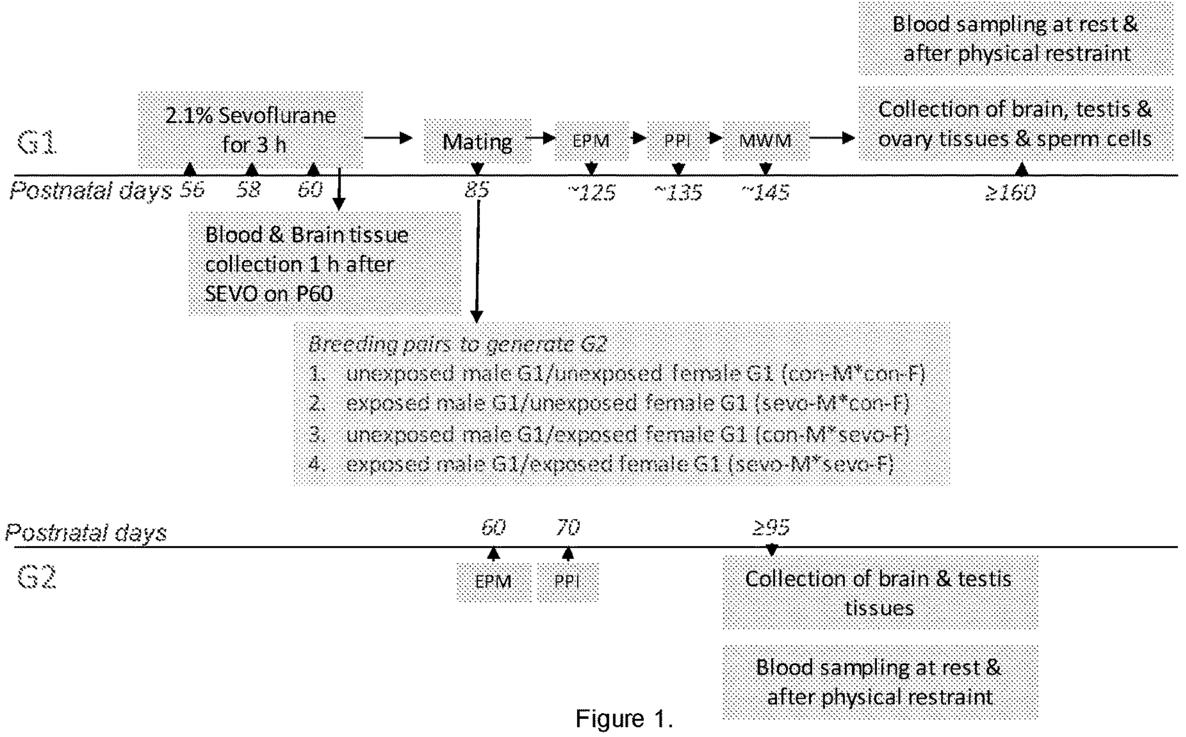
FIG. 1 is an illustration of the study design according to an example of the disclosure.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

In one aspect, disclosed herein is a method for treating a subject having a clinical condition associated with low circulating levels of testosterone, the method including at least the step of administering to the subject a therapeutically effective dose of sevoflurane, thereby treating the clinical condition associated with low circulating levels of testosterone. In a further aspect, the subject can be a mammal such as, for example, a human.

In another aspect, the sevoflurane can be administered via inhalation such as, for example, via a vaporizer. In another aspect, the sevoflurane can be administered nasally.

In various aspects, the sevoflurane can be administered daily for about one day to about 30 days, including any sub-range within the foregoing range. In a particular aspect, the sevoflurane is administered via inhalation. The administration, e.g., via inhalation, can be at a dose level of about 0.05% to about 3% for a period of about 1 minute to about 6 hours, or for about 1, 5, 10, 15, 20, 25, 30, 35, 40, 45, 50, or 55 min, or about 1, 1.5, 2, 2.5, 3, 3.5, 4, 4.5, 5, 5.5, or about 6 hours. In some instances, the administration of sevoflurane can be daily for 1, 2, 3, 4, 5, 6, 7, 8, 9, or 10 days or a combination of any of the foregoing values, or a range encompassing any of the foregoing values (e.g., 2-7 days, 5-10 days, or the like). In another aspect, the administration via inhalation is for a period of time of about 1 minute to about 6 hours at a dose level of about 0.05% to about 3%.

In one aspect, the therapeutically effective dose is from about 0.05 vol % to about 3 vol % when administered via inhalation, or is about 0.05, 0.075, 0.1, 0.25, 0.5, 0.75, 1, 1.25, 1.5, 1.75, 2, 2.25, 2.5, 2.75, or about 3 vol %, or a combination of any of the foregoing values, or a range encompassing any of the foregoing values (e.g., 0.05-2 vol %, 0.05-1 vol %, or the like).

In some aspects, the sevoflurane can be administered via inhalation in oxygen. In another aspect, the sevoflurane can be administered via inhalation in a gas containing about 50 vol % to about 80 vol % $N_2O$, 60 vol % to about 70 vol % $N_2O$, or about 65 vol % $N_2O$ and 25 vol % to about 50 vol % $O_2$, 30 vol % to about 40 vol % $O_2$, or about 35 vol % $O_2$.

In still another aspect, the therapeutically effective dose increases serum levels of testosterone by from about 10% to about 350% within from about 12 hours to about 96 hours following administration. In a further aspect, the therapeutically effective dose increases serum levels of testosterone by about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, or about 350%, or a combination of any of the foregoing values, or a range encompassing any of the foregoing values (e.g., 20% to 270%, 110% to 150%, or the like) as determined by ELISA. In another aspect, the therapeutically effective dose increases serum levels of testosterone within about 12, 16, 20, 24, 28, 32, 36, 40, 44, 48, 52, 56, 60, 64, 68, 72, 76, 80, 84, 88, 92, or about 96 hours following administration, or a combination of any of the foregoing values, or a range encompassing any of the foregoing values (e.g. 16-20 hours, 40-80 hours, or the like).

In one aspect, the therapeutically effective dose increases serum levels of testosterone to about 270 ng/dL to about 1070 ng/dL within about 12 hours to about 96 hours following administration. In a further aspect, the therapeutically effective dose increases serum levels of testosterone to about 270, 300, 350, 400, 450, 500, 550, 600, 650, 700, 750, 800, 850, 900, 950, 1000, 1050, or about 1070 ng/dL, or a combination of any of the foregoing values, or a range encompassing any of the foregoing values (e.g., 300-500 ng/dL, or 450-900 ng/dL, or the like).

In another aspect, the therapeutically effective dose increases serum levels of testosterone in the subject from 1 day to 150 days after the administration of the therapeutically effective dose of sevoflurane. In a further aspect, the therapeutically effective dose increases serum levels of testosterone in the subject for 1 day, 10 days, 20 days, 30 days, 40 days, 50 days, 60 days, 70 days, 80 days, 90 days, 100 days, 110 days, 120 days, 130 days, 140 days, or 150 days after the administration of the therapeutically effective dose of sevoflurane, or a combination of any of the foregoing values, or a range encompassing any of the foregoing values (e.g., 60 days to 120 days, or the like).

In any of these aspects, the clinical condition associated with low circulating levels of testosterone can be Klinefelter's Syndrome, Noonan Syndrome, testicular injury, or congenital anorchidism. In another aspect, the clinical condition associated with low circulating levels of testosterone can be prolactinoma, presence of a pituitary tumor, Prader-Willi syndrome, or Kallmann's syndrome. In still another aspect, the clinical condition associated with low circulating levels of testosterone can be late-onset hypogonadism. In some aspects, more than one of these clinical conditions can be present in the subject simultaneously.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, "administering" can refer to an administration that is oral, nasal, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, or by inhalation. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a state of low circulating testosterone which can be associated with conditions such as hypergonadotropic hypogonadism, hypogonadotropic hypogonadism, or late-onset hypogonadism. The effect can be therapeutic in terms of a partial or complete cure of a disease, condition, symptom or adverse effect attributed to the disease, disorder, or condition. The term "treatment" as used herein can include any treatment of a clinical condition associated with a state of low circulating testosterone, such as hypergonadotropic hypogonadism, hypogonadotropic hypogonadism, or late-onset hypogonadism in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Sevoflurane, as used herein, refers to a compound having the formula $C_4H_3F_7O$. Sevoflurane can also be referred to as 1,1,1,3,3,3-hexafluoro-2-(fluoromethoxy)propane, BAX 3084, fluoromethyl hexafluoroisopropyl ether, fluoromethyl-2,2,2-trifluoro-1-(trifluoromethyl)ethyl ether, sevorane, or Ultane and has the structure:

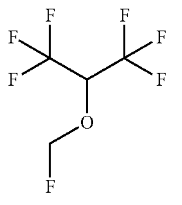 [SMILES: FCOC(C(F)(F)F)C(F)(F)F]

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

In one aspect, the disclosed compositions can be prepared as nasal or inhaled forms. Without wishing to be bound by theory, delivery of the disclosed compounds directly to the lungs and airways by inhalation may reduce the dose of medication required to exert the desired effect due to close contact of the disclosed compositions with the blood vessels of the lungs.

In some aspects, the pharmaceutically acceptable carrier can be an inhalable dry powder. In one aspect, when the pharmaceutically acceptable carrier is a dry powder, it can include glucose, arabinose, maltose, saccharose, dextrose, lactose, mannitol, maltitol, lactitol, sorbitol, or a combination thereof. In another aspect, the carrier particles can have an average particle diameter of from about 0.5 to about 500 μm, or of about 0.5, 1, 2, 3, 4, 5, 6, 7, 8, 9, 10, 20, 30, 40, 50, 100, 150, 200, 250, 300, 350, 400, 450, or about 500 μm, or a combination of any of the foregoing values, or a range encompassing any of the foregoing values. Further in this aspect, aggregate dry powder active ingredients can be converted into an aerosol by airflow during inspiration.

In other aspects, the pharmaceutically acceptable carrier can be saline. In some aspects, if the solution or composition to be nebulized is isotonic or mildly hypotonic, the pharmaceutically acceptable carrier can be sterile water.

In one aspect, the pharmaceutically acceptable carrier can be a high vapor pressure propellant. In another aspect, the pharmaceutically acceptable carrier can be a hydrofluoroalkane (HFA) such as, for example, HFA 134a (1,1,1,2-tetrafluoroethane), HFA 227 (1,1,1,2,3,3,3-heptafluoropropane), HFA 152a (1,1-difluoroethane), or a combination thereof. In an alternative aspect, the pharmaceutically acceptable carrier can be isobutane. In still another aspect, the pharmaceutically acceptable carrier can be a hydrofluoroolefin (HFO) such as, for example, HFO 1234ze (trans-1,3,3,3-tetrafluoroprop-1-ene), HFO 1234yf (2,3,3,3-tetrafluoroprop-1-ene), or a combination thereof. In another aspect, the pharmaceutically acceptable carrier can be a gas or gas mixture including $O_2$, $N_2O$, or any combination thereof.

In one aspect, disclosed herein is a metered dose inhaler or a dry powder inhaler that includes the pharmaceutical compositions disclosed herein. In an alternative aspect, disclosed herein is a nebulizer ampoule that includes the pharmaceutical compositions disclosed herein. In one aspect, nebulizers are advantageous in that large doses of drug can be administered while the patient takes multiple breaths and can be used by patients of any age as breathing does not need to be coordinated with dispensation (as with a metered dose inhaler). In another aspect, nebulizers do not require propellants. However, in some aspects, gas flow such as air or oxygen may be required for aerosolization. In one aspect, the flow can be from about 3.5 to about 8 L/min, or can be about 3.5, 4, 4.5, 5, 5.5, 6, 6.5, 7, 7.5, or about 8 L/min, or a combination of any of the foregoing values, or a range encompassing any of the foregoing values. In another aspect, flow rate can be selected to achieve the desired droplet characteristics (e.g., average particle diameter).

In one aspect, the nebulizer can be a jet nebulizer, an ultrasonic nebulizer, or a mesh nebulizer. In a further aspect, when the nebulizer is a jet nebulizer, it is associated with lower equipment cost and may be capable of delivering drugs that are less effective using a metered dose inhaler. In another aspect, jet nebulizers leave less medication behind as waste than other dosage forms. In some aspects, a jet nebulizer requires pressurized gas to withdraw medication from a reservoir. In some aspects, the jet nebulizer can be a breath-enhanced jet nebulizer. In one aspect, with a breath-enhanced jet nebulizer, more aerosols can be released during inhalation due to negative pressure created by inspiration. In an alternative aspect, the jet nebulizer can be a breath-actuated jet nebulizer. In one aspect, a breath-actuated jet nebulizer is configured to sense breath intake and deliver aerosol only at inspiration.

In one aspect, when the nebulizer is an ultrasonic nebulizer, it may be more efficient at drug delivery than a jet nebulizer. However, in another aspect, an ultrasonic nebulizer may not be able to effectively aerosolize viscous solutions. In some aspects, an ultrasonic nebulizer should not be used with a suspension or a protein.

In still another aspect, when the nebulizer is a mesh nebulizer, it may produce less noise than a jet or ultrasonic nebulizer. In another aspect, a mesh nebulizer has a plate with a plurality of holes, or a mesh, which can be vibrated to produce an aerosol. Further in this aspect, the pharmaceutical composition can be placed above the mesh or plate. In another aspect, when the mesh or plate vibrates, a pumping action begins that extrudes the pharmaceutical composition through the mesh or plate as aerosols, wherein the aerosol particle size is determined by the diameter of the holes or mesh screen.

In any of these aspects, an aerosol particle size of less than about 9 μm, or of less than about 5 μm is created by the nebulizer or inhaler. In some aspects, the particle size can be about 2, 2.5, 3, 3.5, 4, 4.5, 5, 5.5, 6, 6.5, 7, 7.5, 8, 8.5, or about 9 μm, or a combination of any of the foregoing values, or a range encompassing any of the foregoing values. In any of these aspects, average treatment time with a nebulizer can be from about 5 min to about 8 min, or can be about 5, 6, 7, or about 8 min, or a combination of any of the foregoing values, or a range encompassing any of the foregoing values. In one aspect, average active ingredient output for a nebulizer can be from about 400 to about 500 mg/min, or can be about 400, 410, 420, 430, 440, 450, 460, 470, 480, 490, or about 500 mg/min, or a combination of any of the foregoing values, or a range encompassing any of the foregoing values. In another aspect, when two or more active ingredients are included in the compositions, the active ingredients can be delivered by the nebulizer at different rates.

In another aspect, the disclosed compositions can be delivered nasally. In one aspect, nasal administration can be accomplished using a nebulizer as disclosed previously accompanied by a mask that can be fitted to the face of a subject to enable nasal breathing. In an alternative aspect, nasal sprays and other nasal delivery mechanisms are inexpensive, portable, and easy to use and may help ensure patient compliance with treatment. In one aspect, nasal delivery can be accomplished using a pressurized metered-dose inhaler or a metered-dose spray pump. In some aspects, delivery location of nasally administered compositions is affected by particle size. In one aspect, particles larger than about 10 μm remain primarily in the nose and sinuses, whereas particles smaller than about 9 μm are capable of traveling to the upper airways and into the lungs.

In one aspect, when the pharmaceutical compositions are delivered nasally, they can be aqueous solutions, suspensions, powders, gels, and/or emulsions. In another aspect, when the pharmaceutical compositions are delivered via metered-dose spray pumps or via other multi-dose containers (e.g., side-actuated spray pumps), the pharmaceutical compositions can include a preservative such as, for example, benzalkonium chloride. In some aspects, nasally delivered pharmaceutical compositions may be packaged as drops, as compositions to be vaporized (e.g., menthol vapor inhalers for the common cold), as breath powered or hand-actuated spray pumps or drop dispensers, in electrically powered nebulizers or atomizers, by hand-actuated powder sprayers, by insufflators, squeeze bottles, or the like. In some aspects, nasally administered pharmaceutical compositions as disclosed herein can be deposited in the nose by medical personnel using a catheter or micropipette.

In any of these aspects, various excipients can be added to nasally-delivered pharmaceutical compositions including, but not limited to, co-solvents (e.g., alcohols including ethanol, propylene glycol), osmotic pressure or tonicity regulators (e.g., dextrose, sodium chloride), buffers and pH adjustment compounds (trisodium citrate, hydrochloric acid, sodium hydroxide, sulfuric acid), preservatives (e.g., benzyl alcohol, benzalkonium chloride, chlorobutanol, methylparaben, phenylethyl alcohol, propylparaben, and related compounds), antioxidants (e.g., butylated hydroxyanisole), suspending agents and/or stabilizers (e.g., microcrystalline cellulose, sodium carboxymethyl cellulose), chelating agents (e.g. sodium EDTA), penetration enhancers (e.g., oleic acid), surfactants (e.g., PEG400, PEG 3500, polyoxyl 400 stearate, polysorbate 20, polysorbate 80), and combinations thereof.

In any of these aspects, administration via nasal delivery or inhalation may enable rapid onset of action for the compositions disclosed herein.

In various aspects, the present disclosure pertains to methods of treating a subject having a clinical condition associated with low-circulating testosterone, the method comprising a therapeutically effective dose of sevoflurane. In some instances, the disclosed method provides administration sufficient to achieve mild sedation in the subject. In other aspects, the administering is non-invasive and occurs via inhalation.

The disclosed methods of treatment are believed to provide a clinically significant increase in serum testosterone with no obvious side effects on fertility and reproduction.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

ASPECTS

The present disclosure can be described in accordance with the following numbered aspects, which should not be confused with the claims.

Aspect 1. A method of treating a subject having a clinical condition associated with low circulating levels of testosterone, comprising:

administering to the subject a therapeutically effective dose of sevoflurane, thereby treating the clinical condition associated with low circulating levels of testosterone.

Aspect 2. The method of aspect 1, wherein the administering is via inhalation.

Aspect 3. The method of aspect 2, wherein the inhalation is via administration a vaporizer.

Aspect 4. The method of aspect 1, wherein the administering is nasally.

Aspect 5. The method of any one of aspects 1-4, wherein the therapeutically effective dose increases serum levels of testosterone in the subject from 1 day to 150 days after the administration of the therapeutically effective dose of sevoflurane.

Aspect 6. The method of any one of aspects 1-4, wherein the therapeutically effective dose increases serum levels of testosterone by about 10% to about 350% within about 12 hours to about 96 hours following administration.

Aspect 7. The method of any one of aspects 1-4, wherein the therapeutically effective dose increases serum levels of testosterone to about 270 ng/dL to about 1070 ng/dL within about 12 hours to about 96 hours following administration.

Aspect 8. The method of any one of aspects 1-7, wherein the administering comprises daily administration for about one day to about 10 days.

Aspect 9. The method of any one of aspects 1-8, wherein the therapeutically effective dose is about 0.05 vol % to about 3 vol % when administered via inhalation.

Aspect 10. The method of aspect 9, wherein the therapeutically effective dose is about 0.05 vol % to about 2 vol % when administered via inhalation.

Aspect 11. The method of aspect 9, wherein the therapeutically effective dose is about 0.05 vol % to about 1 vol % when administered via inhalation.

Aspect 12. The method of any one of aspects 1-11, wherein the sevoflurane is administered via inhalation in oxygen.

Aspect 13. The method of any one of aspects 1-11, wherein the sevoflurane is administered via inhalation in a gas comprising about 50 vol % to about 80 vol % $N_2O$, about 60 vol % to about 70 vol % $N_2O$, or about 65 vol % $N_2O$ and about 25 vol % to about 50 vol % $O_2$, about 30 vol % to about 40 vol % $O_2$, or about 35 vol % $O_2$.

Aspect 14. The method of any one of aspects 1-11, wherein the clinical condition associated with low circulating levels of testosterone is Klinefelter's Syndrome, Noonan Syndrome, testicular injury, or congenital anorchidism.

Aspect 15. The method of any one of aspects 1-11, wherein the clinical condition associated with low circulating levels of testosterone is prolactinoma, presence of a pituitary tumor, Prader-Willi syndrome, or Kallmann's syndrome.

Aspect 16. The method of any one of aspects 1-11, wherein the clinical condition associated with low circulating levels of testosterone is late-onset hypogonadism.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Background: Each year millions of patients have surgeries under general anesthesia. Anesthetic exposure in early childhood or old age is linked to neurocognitive deficiencies, but young adults are presumed resistant to such effects and hence are rarely studied.

Methods: To investigate potential transgenerational effects of young adult anesthetic exposure, postnatal day 56 rats (generation 1, G1) were sevoflurane anesthetized on 3 alternate days and mated 25 days later to produce offspring (generation 2, G2).

Results: The G1 males and females had elevated systemic corticosterone, but only males had decreased hypothalamic cell surface $K^+$-$2Cl^-$ (KCC2) $Cl^-$ exporter expression 1 h after the last sevoflurane exposure. Only G1 males exhibited persistent neurobehavioral deficiencies, exaggerated hypothalamic-pituitary-adrenal (HPA) axis responses to restraint, elevated levels of testosterone and reduced testis weight. Changes in hypothalamic-pituitary-testicular (HPT) axis functioning and expression of hypothalamic aromatase and estrogen receptors were consistent with a role for systemic testosterone/brain estradiol in G1 sex-specific effects of sevoflurane. Only the male offspring of exposed parents (G2) exhibited neurobehavioral deficiencies, but had unaltered HPA and HPT axis functioning. Finally, down-regulated Kcc2 expression in G1 and G2 male hypothalamus and hippocampus, and hyper-methylated Kcc2 promoter in G1 sperm and ovary and G2 male hypothalamus and hippocampus support the involvement of epigenetic mechanisms in sevoflurane's intergenerational effects.

Conclusions: Repeated exposure of young adult rats to sevoflurane results in sex-specific central and systemic abnormalities, some of which are passed to offspring, which could increase risk for disease later in life.

Introduction

According to 2016 World Health Organization estimates, the number of surgeries performed globally rose from 226.4 million in 2004 to 312.9 million in 2012.[1] This progress would not be possible without modern general anesthesia, which can be viewed as a state of pharmacologically induced "reversible brain coma". 2 Despite advancements in refining anesthesia approaches, multiple studies support the contention that the effects of general anesthetics are not completely reversible upon anesthesia withdrawal. 3 Neurocognitive deficiencies attributed to anesthesia may persist in neonates or endure for weeks to years in the elderly. 3,4 In contrast to these adverse effects at the extreme ends of the lifespan (when the brain may be at its most vulnerable), potential adverse effects of anesthesia in young adults remain essentially unexplored.

Sevoflurane, propofol and etomidate, anesthetics that positively modulate GABA type A receptor (GABA A R) functioning, may induce developmental effects in neonatal rodents similar to those induced by repeated maternal separation stress.[5-7] Consistent with such stressor-like effects, a single episode of GABAergic anesthesia in neonatal rats is sufficient to cause multifold increases in corticosterone secretion at the time of anesthesia.[6,7] After maturing to adulthood, these rats exhibit exacerbated hypothalamic-pituitary-adrenal (HPA) axis responses to stress among other abnormalities. 5-7 Anesthetic-altered, age-dependent GABA A R signaling may contribute to initiation and mediation of these abnormalities. GABA A R signaling is excitatory during early life due to elevated levels of intraneuronal $Cl^-$, maintained by relatively low and high levels of the $K^+$-$2Cl^-$ (KCC2) $Cl^-$ exporter and $Na^+$-$K^+$-$2Cl^-$ (NKCC1) $Cl^-$ importer, respectively. During the second postnatal week in rats, GABA A R signaling gradually becomes inhibitory, primarily due to age-dependent increases in KCC2.[8,9] The magnitude of GABA A R excitatory signaling and the proper timing of its transition from excitatory to inhibitory are key for normal brain development, and impairments in KCC2 and resulting shifts in GABA A R signaling toward excitatory have been linked to several neuropsychiatric disorders in both humans and animal models.[10-12] Exposure to GABAergic anesthetics appears to enhance the magnitude of $GABA_AR$ excitatory signaling and to disrupt the normal development of the excitatory-to-inhibitory shifts in GABA A R signaling. In support of this contention, adult rats exposed to anesthesia as neonates have down-regulated Kcc2 expression, and NKCC1 inhibition prior to anesthetic exposure alleviates anesthesia-induced developmental abnormalities.[5,13]

Interestingly, recent evidence suggests that developmental consequences of GABAergic anesthetics may be sex-dependent—with greater effects in males than females—and furthermore, that these developmental consequences can be transmitted intergenerationally via epigenetic mechanisms.[5,14] Anesthetic-induced impairments in Kcc2 may contribute to mediation of these intergenerational effects.[5]

In adult mice and rats, both acute and chronic stress induce dephosphorylation of the KCC2 Ser940 residue, leading to a decrease in KCC2 cell surface expression and a shift in $GABA_AR$ signaling from inhibitory to excitatory in the paraventricular nucleus (PVN) of the hypothalamus, the ventral tegmental area and the hippocampus.[15-18] Given that sevoflurane acts as a stressor in neonatal rats and initiates developmental abnormalities, at least in part, by potentiating excitatory GABA A R signaling,[5,7] here we tested whether sevoflurane has comparable effects in young adult rats. Specifically, we evaluated whether young adult exposure to sevoflurane induces a stress response, alters Kcc2 expression and behavior, and whether these effects are sex-dependent and/or transmitted intergenerationally.

Methods and Materials

Animals

All experimental procedures were approved by the University of Florida Institutional Animal Care and Use Committee. Sprague-Dawley rats were bred at the University of Florida animal care facility. The rats were housed under controlled illumination (12-h light/dark, lights on at 7:00 a.m.) and temperature (23-24° C.) with free access to food and water. Within 24 h of delivery, litters were culled to 12 pups. At the age of 21 days, pups were weaned and housed in sex-matched pairs for the remainder of the study.

Treatment Groups

Male and female rats in Generation 1 (G1) underwent anesthesia on postnatal days 56, 58 and 60. During this period, rats were held in a temperature-controlled chamber (+37° C.) with a continuous supply of 30% oxygen in air (1.5 L/min) during anesthesia—6% sevoflurane for 3 min for anesthesia induction and 2.1% sevoflurane for 177 min for anesthesia maintenance (the Sevoflurane group). Gas monitoring was performed using a calibrated Datex side stream analyzer (Datex-Ohmeda, Helsinki, Finland), which samples from the animal chamber interior. Rats in the G1 control group (Control) were not subjected to anesthesia. A subset of the rats in the G1 Control and Sevoflurane groups was sacrificed 1 h after the last exposure to sevoflurane (or equivalent timepoint in the Control group) to collect blood and brain tissue samples. FIG. 1 provides a schematic of experimental design. The remaining Control and Sevoflurane G1 male and female rats were mated on P85 to produce offspring (generation 2, G2). Only rats from different litters were mated. G2 rats were categorized as the offspring of: 1) control males+control females (con-M*con-F); 2) exposed males+control females (sevo-M*con-F); 3) control males+ exposed females (con-M*sevo-F); and 4) exposed males+ exposed females (sevo-M*sevo-F). The females were kept alone throughout the entire gestation and post-partum rearing periods.

Sixty-four G1 rats (32 control and 32 sevoflurane exposed) and 122 G2 rats, which were not exposed to sevoflurane anesthesia and were subjected to animal facility rearing only, were studied. The G1 rats were sequentially evaluated in the EPM starting on ~P125, PPI of the acoustic startle response on ~P135 and MWM starting ~on P145 (FIG. 1). One half of these animals were sacrificed on ≥P160 to collect trunk blood, brain and testis and ovarian tissues for further analyses. The rest of these animals were physically restrained for 30 min on ≥P160 to measure corticosterone responses, followed by collection of tissue samples (as above) for further analyses. The G2 rats were evaluated in the EPM starting on P60 and PPI of startle on P70 (FIG. 1). One half of these animals were sacrificed on ≥P95 to collect trunk blood and brain tissue samples for further analyses, and the rest of these animals were tested for the corticosterone responses to physical restraint for 30 min on ≥P95 before collecting the trunk blood and brain tissue samples.

Behavioral Tests

Assessment of Behavior in the Elevated Plus Maze (EPM)

The EPM studies were performed using an EPM apparatus and BIO-EPM 3C video tracking software (EB Instruments, Pinellas Park, FL) during the light phase of the dark-light cycle as previously described by our laboratory.[5-7] If a fall occurred, the animal was removed from the study (one G1 male rat was removed from the study for this reason).

Measurements of the Prepulse Inhibition (PPI) of Startle

The PPI of startle tests were performed using a SR-Lab startle apparatus (San Diego Instruments, San Diego, CA) as previously described.[5-7] The % PPI for each prepulse level was calculated using the following formula: % PPI=100× [(pulse alone)−(prepulse+pulse)]/pulse alone. Data were collected as $V_{max}$ amplitude.

The Morris Water Maze (MWM) Test

The MWM tests were run using a MWM apparatus and data were analyzed using a computer-based video tracking system (Water 2020; HVS Image) as previously described. 5

Basal and Stress-Induced Activity of the HPA Axis.

Blood samples (~300 μl) were collected using the "tail clip" method at rest and 10, 60, and 120 min after the restraint. Physical restraint was administered using rodent holders (Kent scientific Corporation, Torrington, CT). Serum corticosterone was measured using commercial ELISA kits (Cayman Chemical Company, Ann Arbor, MI, USA) according to the manufacturer's instructions.

Tissue Collection

After decapitation, the trunk blood samples were collected and centrifuged at 4° C., 1000 g for 15 min, and then kept at −80° C. for hormone assays. The brain was removed from the skull onto ice pads. The hypothalamus was isolated by making an anterior cut at the level of the optic chiasm, a posterior coronal section anterior to the mammillary bodies, two sagittal cuts parallel to the lateral ventricles and a dorsal horizontal cut at the level of the anterior commissure, as described elsewhere.[19] The hippocampus was isolated from the respective blocks. All tissue samples were placed in vials filled with RNAlater solution (Invitrogen, Carlsbad, CA) and then stored at −80° C. Testis tissue was removed and washed with 0.9% saline before weighing. Sperm were isolated from the caudal epididymis of adult males into PBS with 1% BSA at 37° C. using a swim-up assay. After settling for 30 min, sperm-containing supernatant was centrifuged for 5 min at 4000 rpm. Sperm pellets were stored at −80° C. After separation from the adipose tissues, ovaries were stored at −80° C.

Measurements of serum follicle stimulating hormone (FSH), luteinizing hormone (LH), testosterone (Tn) and estradiol (E2) levels.

Hormone analyses in serum samples isolated from G1 and G2 rats were performed using commercially available kits according to the manufacturer's instructions. Serum concentrations of FSH (CSB-E06869r) and LH (CSB-E12654r) were quantified using ELISA kits (CUSABIO TECHNOLOGY LLC, Houston, TX, USA). Serum Tn and E2 concentrations were measured using ELISA kits (582701, Cayman Chemical Company, Ann Arbor, MI, USA and ES180S-100, Calbiotech, Spring Valley, CA, USA, respectively).

Analyses of mRNA levels for corticotropin-releasing hormone (Crh), glucocorticoid receptors (Grs), estrogen receptor α (Erα), estrogen receptor β (Erβ), aromatase, gonadotropin-releasing hormone (Gnrh), Nkcc1, and Kcc2

Levels of mRNA for Nkcc1 and Kcc2 in the hypothalamus and hippocampus, for Crh, Erα, Erβ, aromatase, GnRH in the hypothalamus, and for Grs in the hippocampus were analyzed via reverse transcription-PCR (qRT-PCR) in a StepOnePlus™ Real-Time PCR System (Applied Biosystems, Foster City, CA) as previously described. 5 RNA was extracted from the samples using an RNeasy Plus Kit (Qiagen, Valencia, CA), reverse transcribed with a highcapacity cDNA reverse transcription kit (Bio-Rad Laboratories, Hercules, CA), and then analyzed via qRT-PCR. Taqman probes specific for the above genes were obtained from Applied Biosystems (Carlsbad, CA): Crh (Rn01462137_m1), Gr (Rn00561369_m1), Erα (Rn01430446_m1), Erβ (Rn00562610_m1), aromatase (Rn00567222_m1), Gnrh (Rn00562754_m1), Nkcc1 (Rn00582505_m1) and Kcc2 (Rn00592624_m1). Data were normalized to glyceraldehyde-3-phosphate dehydrogenase (Gapdh) mRNA (Rn01775763_g1). Gene expression was calculated using the ΔΔCT method and data are presented as relative fold change from that of control animals.

Bisulfite Sequencing

Genomic DNA was extracted from the sperm pellet and ovaries of adult G1 rats and from hippocampal and hypothalamic tissues of G2 rats using the DNeasy Blood and Tissue kit (Qiagen, Hilden, Germany). The sodium bisulfite conversion was performed with EZ DNA Methylation kits (Zymo Research, Irvine, CA) following the manufacturer's instructions. The primers (Kcc2: forward: GATTGTAAGTGTTTTTATTATTGAGTTGTATATT (SEQ ID NO: 1); reverse: AATAAACTTTTCCCCTTTTATACCC (SEQ ID NO: 2) were designed for the bisulfite-converted DNA sequences, using previously published sequences. 5 PCR amplification was performed with HotStar Taq (Qiagen, Hilden, Germany). Amplicons were cloned into pCR4-TOPO vector with the TOPO TA cloning kit for sequencing (Life Technologies, Carlsbad, CA). Miniprep was performed on each positive clone using ZR Plasmid Miniprep kit (Zymo Research, Irvine, CA). Sanger sequencing was done by Genewiz (South Plainfield, NJ, USA) using M13R primers. The DNA methylation status of all CpG sites was analyzed using Benchling Molecular Biology 2.0 Software (Benchling, San Francisco, CA). The bisulfite sequencing analysis of the Kcc2 DNA was performed only in G2 male progeny of con-M*con-F and sevo-M*sevo-F matings.

Immunohistochemistry

Rats were anesthetized with sevoflurane and transcardially perfused with saline, followed by 4% paraformaldehyde (PFA) in 0.1 M phosphate buffer. The brains were collected and fixed in the 4% PFA overnight and then dehydrated in 30% sucrose solution in PBS at 4° C. for 2 days. The brains were cut into 18-um-thick coronal sections using a cryostat. After blocking with 10% norm goat serum for 1 h at room temperature, the slices were incubated with the primary antibody (rabbit anti-KCC2, 1:500; MilliporeSigma, Burlington, MA) in 10% norm goat serum at 4° C. overnight. After washing with PBS for 3×5 min, the slices were exposed to the secondary antibody, Alexafluor 549 goat anti-rabbit (Invitrogen, Carlsbad, CA). Slides were then washed with PBS for 3×5 min and incubated for 10 min at room temperature with DAPI (1:1000; Sigma, St. Louis, MO) in PBS for 10 min. The sections were mounted and covered with coverslip after washing with PBS for 3×5 min. A confocal microscope (IX2-DSU spinning disk confocal fluorescent microscope system, Olympus, Tokyo, Japan) was used to capture the fluorescent images. The immunofluorescence intensity of the KCC2-immunoreactive cells was measured using ImageJ software [National Institutes of Health (NIH)]. Three images from the PVN of the hypothalamus of each animal were taken and the average intensity values were calculated to use for statistical analysis.

Statistical Analysis

Statistical analyses were conducted on raw data using SigmaPlot 14.0 software (Systat Software, Inc., San Jose, CA), which automatically checks if data set meets test criteria (Shapiro-Wilk for normality test and Brown-Forsythe for Equal Variance Test). Values are reported as mean±SE. The primary outcome in this study was the neurobehavioral changes in offspring of rats exposed to sevoflurane in young adulthood. All other outcome measures were the secondary outcomes. One F0 male rat was removed from the EPM study because of a fall from the maze. Another F0 male rat in the control group was removed from the behavioral studies because of injury while matting with a female rat. Outliers were identified using boxplots. If an outlier was not in the plausible range of values for the outcome (indicating measurement or recording error) it was removed; all other values were maintained in analyses. Occurrence of outliers in outcomes was rare. An unpaired t-test was used to analyze F0 data for serum corticosterone levels and cell surface KCC2 expression 1 h after the last exposure to sevoflurane, EPM, testis weight, hormone levels for Tn, E2, LH and FSH and gene expression for Crh, Grs, Erα, Erβ, Aromatase, GnRH, Nkcc1 and Kcc2. To analyze F1 data for EPM, testis weight, Tn level and gene expression for Crh, Grs, Nkcc1 and Kcc2, one-way ANOVA was used. A two-way repeated measures ANOVA was used to analyze the PPI data, with the treatment and prepulse intensity as independent variables. A two-way repeated measures ANOVA was used to analyze acquisition (escape latency) in the MWM, with experimental groups and days of training as the independent variables. An unpaired t-test was used to analyze time spent in the target quadrant and numbers of crossings during the MWM probe test. A two-way repeated measures ANOVA was used to analyze changes in serum corticosterone levels at rest and at 3 time points after the restraint, with experimental groups and time as the independent variables. To assess differences in total corticosterone concentrations, area under the curve with respect to baseline (AUCg, levels of corticosterone at rest), was calculated and compared across experimental groups using an unpaired t-test. Two-way measures ANOVA with treatment as between'-subject factor and CpG site as 'within'-subject factor was used to analyze data on the frequency methylation of CpG sites in the Kcc2 gene promoter in F0 and F1 tissue samples. An unpaired t-test was used to analyze DNA methylation level at all 6 CpG sites. All multiple pairwise comparisons were done with the Holm-Sidak method. All comparisons were run as two-tailed tests. P≤0.05 was considered significant. Statistical details are presented in text and in figure legends. The sample sizes in this study were based on previous experience with the same experimental techniques,[12,13,23,24] which were further confirmed by a power analysis using SigmaPlot 14.0 software.

Results

Figures 2, 2A, 2B, 2C, 2D, 2E, 2F:
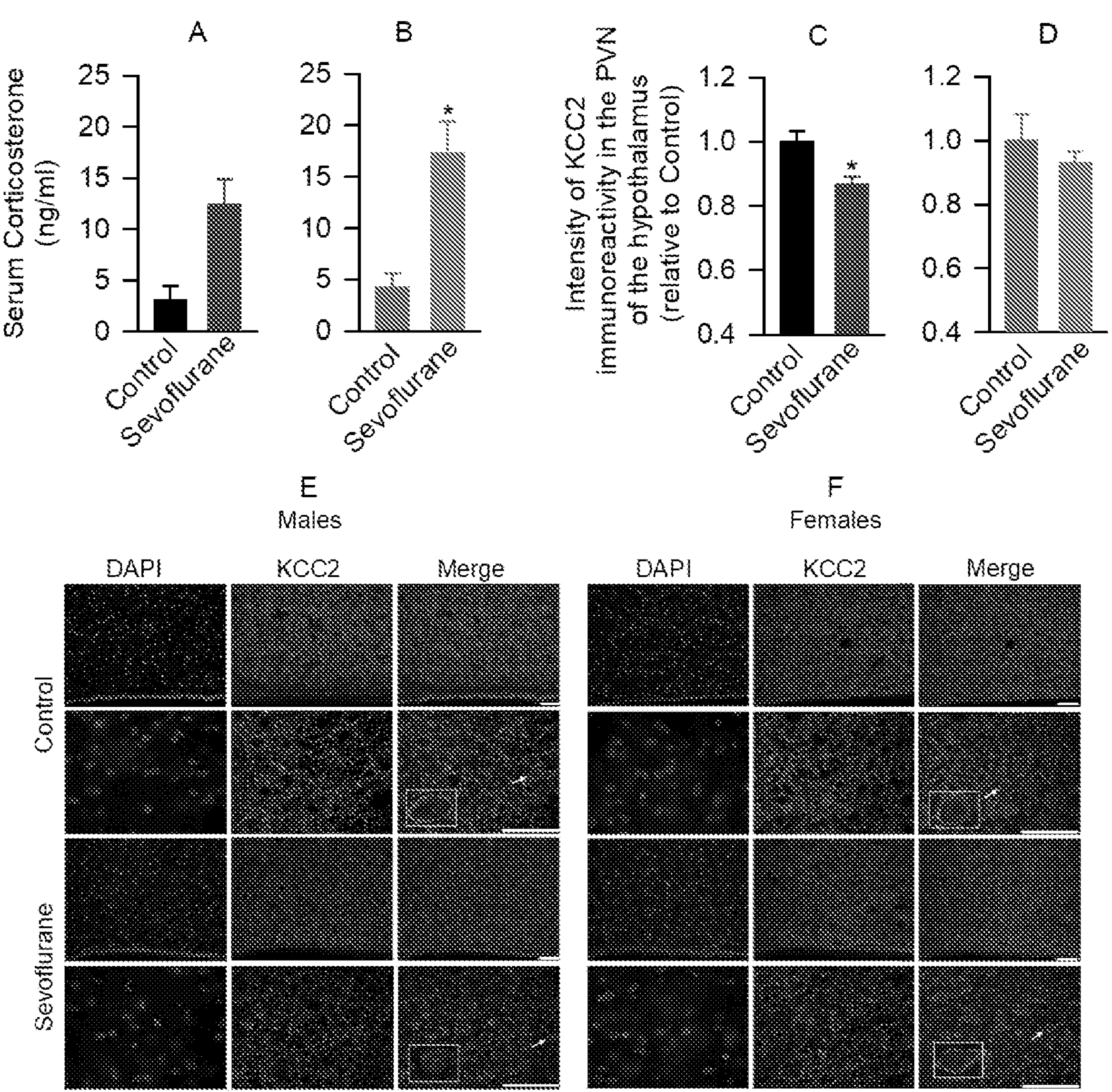
FIGS. 2A-2F demonstrate that G1 male and female rats had elevated systemic corticosterone, but only male rats had decreased hypothalamic cell surface K+-2Cl—(KCC2) Cl- exporter expression 1 h after the sevoflurane exposure on postnatal day 60. The rats were exposed to sevoflurane for 3 h on postnatal days (P) 56, 58 and 60.

Acute effects of repeated exposures of young adult rats to sevoflurane. To measure acute effects of sevoflurane, rats were exposed to 2.1% sevoflurane anesthesia for 3 h on P56, P58 and P60. Brain tissue and trunk blood samples were collected 1 h after sevoflurane anesthesia on P60. Turning now to FIGS. 2A-2F, it is shown that the G1 male and female rats had elevated systemic corticosterone, but only male rats had decreased hypothalamic cell surface $K^+$-$2Cl^-$ (KCC2) $Cl^-$ exporter expression 1 h after the sevoflurane exposure on postnatal day 60. The rats were exposed to sevoflurane for 3 h on postnatal days (P) 56, 58 and 60. (FIGS. 2A, 2B) Shown are the respective levels of serum corticosterone in G1 male (A) and female (B) rats. Data are means±SEM (n=4 and n=5 per treatment group in males and females, respectively). *P<0.05 vs. Control. (FIGS. 2C-2F) Representative confocal images and quantitative analysis of the KCC2 immunoreactivity in the paraventricular nucleus (PVN) of the hypothalamus of the control and sevoflurane-exposed male (FIGS. 2C, 2E) and female (FIGS. 2D, 2F) rats. FIG. 2E provides representative confocal images of the PVN from the control (CON) and sevoflurane-exposed (SEVO) male rats, immunostained for DAPI (left; blue) and KCC2 (middle; red); the merge column shows colocalized images (right; red and blue) (FIG. 2F). The arrowheads indicate the cells shown in the boxed areas at higher magnifications. The KCC2 immunoreactivity, located on the periphery of the neurons (red color), decreased in the PVN neurons from the sevoflurane-exposed male rats. Similar representative confocal images of the PVN from the control (CON) and sevoflurane-exposed (SEVO) female rats shown in (FIG. 2F). Scale bars, 50 μm. The sevoflurane-exposed males, but not sevoflurane-exposed females, had reduced cell surface KCC2 expression (*P<0.05 vs. Control; FIG. 2C, 2E). Data are means±SEM (n=4 per treatment group).

Consistent with the stress-like effects of sevoflurane reported in previous work,[7] the exposed male and female rats had significantly increased serum levels of corticosterone compared to controls ($t_{(6)}$=−3.313; P=0.0162, males, FIG. 2A; and $t_{(8)}$=−3.949; P=0.00424, females, FIG. 2B). Despite similar increases in corticosterone levels in sevoflurane-exposed males and females, immunofluorescence evaluations of cell surface KCC2 expression in the PVN of the hypothalamus found reductions in KCC2 density in male ($t_{(6)}$=3.343; P=0.0156), but not female ($t_{(6)}$=0.773; P=0.469), G1 rats (FIGS. 2C-2F).

Figures 3A, 3W:
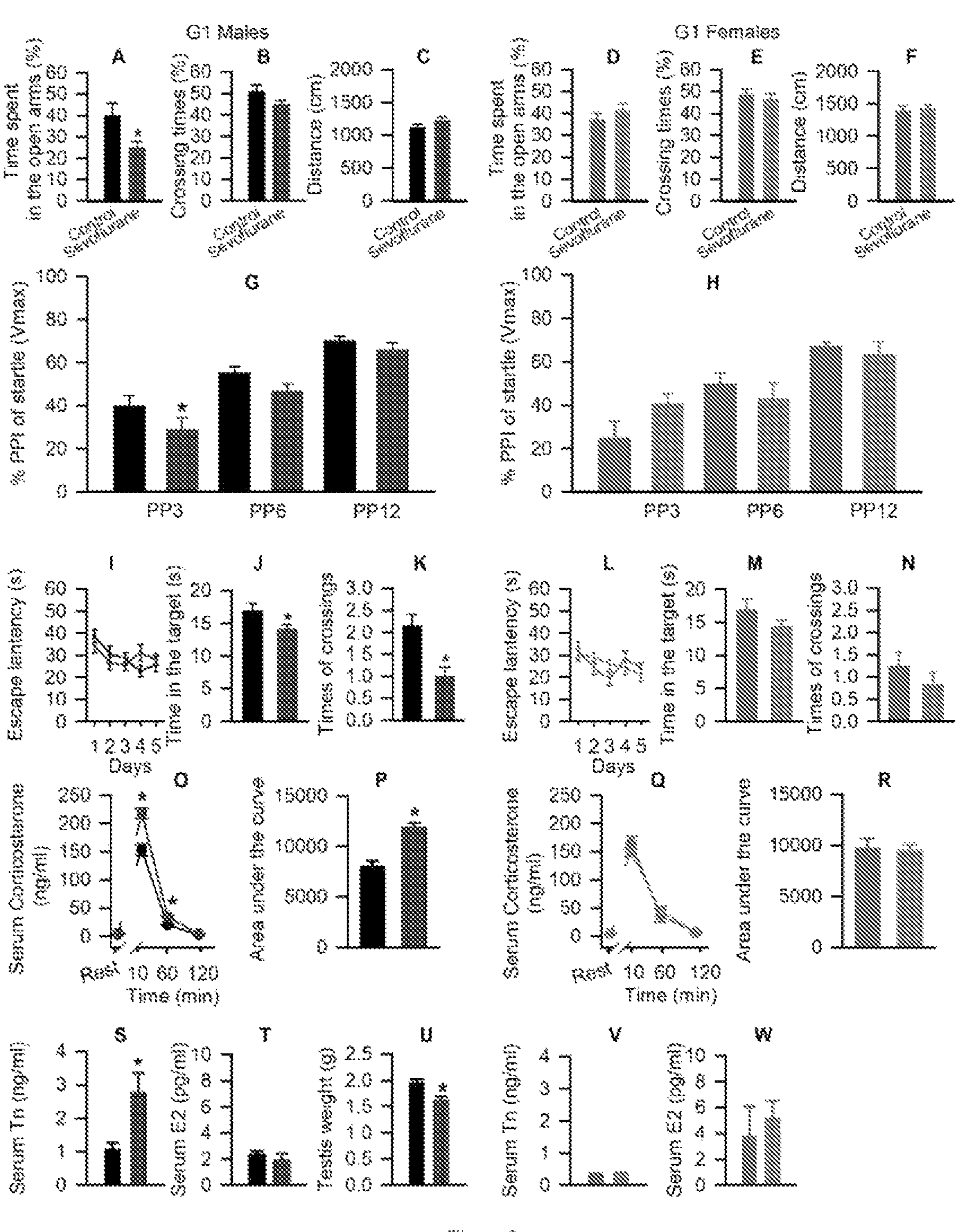
FIGS. 3A-3W are graphs illustrating that G1 male, but not female, rats, exposed to sevoflurane for 3 h on postnatal days (P) 56, 58 and 60, exhibited long-term behavioral abnormalities, exacerbated corticosterone responses to stress, elevated serum levels of testosterone and reduced testis weight. Shown are % of time spent in open arms of the elevated plus maze, number of crossing the open arms, and distance traveled by male (A-C) and female (D-F) rats.

Long-term systemic effects of repeated exposure of young adult rats to sevoflurane. As shown in FIGS. 3A-3W, G1 male, but not female, rats, exposed to sevoflurane for 3 h on postnatal days (P) 56, 58 and 60, exhibited long-term behavioral abnormalities, exacerbated corticosterone responses to stress, elevated serum levels of testosterone and reduced testis weight. Shown are % of time spent in open arms of the elevated plus maze, number of crossing the open arms, and distance traveled by male (FIGS. 3A-3C) and female (FIGS. 3D-3F) rats. Data are means±SEM from 15 male and 16 female rats per treatment group. (FIGS. 3G, 3H) Shown are % PPI responses at prepulse intensity of 3 dB, 6 dB and 12 dB in male (FIG. 3G) and female (FIG. 3H) rats. Data are means±SEM from 15 males in the Control group, 16 males in the Sevoflurane group and 16 females per treatment group. *P<0.05 vs. Control. FIG. 3I provides plots showing the values of escape latencies during the 5-day training period for G1 male rats. FIGS. 3J, 3K are histograms showing the time spent in the target quadrant and the number of times that a rat crossed the previous location of the escape platform. FIGS. 3L-3N are histograms showing respective data for G1 female rats collected during the MWM tests. n=12 for each treatment group (*P<0.05 vs. G1 males from the Control group). In FIGS. 3O-3R, shown are the respective levels of serum corticosterone across each collection point, as well as the total corticosterone responses (AUCg) in male (FIGS. 3O, 3P) and female (FIGS. 3Q, 3R) rats. Serum levels of corticosterone at rest were taken as baselines for calculations of the total corticosterone responses. Data are means±SEM from 8 rats per treatment group. In FIGS. 3S-3U, shown are serum levels of testosterone (FIG. 3S), estradiol (FIG. 3T) and testis weight (FIG. 3U) in G1 male rats. (FIGS. 3U, 3W) Serum levels of testosterone and estradiol in G1 female rats. Data are means±SEM from 8 rats per treatment group. Data of testis weight are from 16 rats in control group and 13 rats in sevoflurane group. *P<0.05 vs. Control. Color coding of experimental groups in FIGS. 3A-3F is applicable to all figures.

More than two months after exposure to sevoflurane anesthesia, G1 male rats spent less time in open arms ($t_{(28)}$=2.18; P=0.0378; FIG. 3A), but did not differ from their control counterparts in number of crossings ($t_{(28)}$=1.456; P=0.157; FIG. 3B) or distance traveled ($t_{(28)}$=−1.351; P=0.188; FIG. 3C) during the EPM test. In G1 females, there was no significant between-subjects effect of anesthesia with sevoflurane on any of these EPM parameters (FIGS. 3D-3F).

As in the EPM task, there was a significant effect of sevoflurane exposure on PPI of startle in adult G1 male rats ($F_{(1,123)}$=6.765; P=0.01; FIG. 3G), but not in G1 female rats ($F_{(1,60)}$=0.0488; P=0.827; FIG. 3H). Multiple pairwise comparisons indicated that exposure to sevoflurane led to impaired PPI of startle responses in G1 male rats at prepulse intensity of 3 dB (P=0.042 vs control). Startle stimuli by themselves caused similar responses in the control and sevoflurane groups of G1 male ($t_{(41)}$=−0.969; P=0.338) and G1 female ($t_{(30)}$=1.465; P=0.153) rats.

In males, the MWM test showed no significant between-subjects effect of sevoflurane exposure on escape latencies across the 5-day training period ($F_{(1,88)}$=0.00767, P=0.931), although, as expected, there was a significant within-subjects effect of day of training ($F_{(4,88)}$=3.842, P=0.006) (FIG. 3I). In contrast, male rats from the sevoflurane group spent significantly less time in the target quadrant of the MWM ($t_{(22)}$=2.185; P=0.0398, FIG. 3J) and made fewer crossings over the escape platform location ($t_{(22)}$=3.626; P=0.00150, FIG. 3K). There were no significant group effects in the MWM tests of G1 female rats (FIG. 3L-N).

To assess long-term effects of young adult sevoflurane anesthesia on systemic levels of corticosterone at rest and after exposure to an acute stressor, serum corticosterone levels were measured in blood samples collected prior to physical restraint and 10, 60 and 120 min after the restraint. Male rats had significantly higher total corticosterone responses when compared to their control counterparts (measured as AUCg) ($t_{(14)}$=−6.209; P<0.001; FIGS. 3O, 3P). This increase was due to higher levels of corticosterone at 10 min (P<0.001 vs control) and 60 min (P=0.036 vs control) after restraint, as serum levels of corticosterone before the restraint (P=0.736 vs control) and 120 min (P=0.787 vs control) post restraint were not different in control and sevoflurane exposed rats (FIG. 3O). There was no difference in serum corticosterone levels between control and sevoflurane-exposed G1 female rats (FIGS. 3Q,3R).

The G1 male rats had significantly increased serum levels of Tn ($t_{(14)}$=−2.839; P=0.0131; FIG. 3S), but not serum levels of E2 ($t_{(14)}$=0.703; P=0.494; FIG. 3T) more than 3 months after sevoflurane exposure. Sevoflurane-exposed G1 males also had significantly reduced testis weight ($t_{(27)}$=4.494; P=0.000119; FIG. 3U). The G1 female rats in the sevoflurane and control groups were not different with respect to serum levels of Tn ($t_{(14)}$=−0.347; P=0.743; FIG. 3V) or E2 ($t_{(18)}$=−0.537; P=0.600; FIG. 3VV).

Figures 4A, 4P:
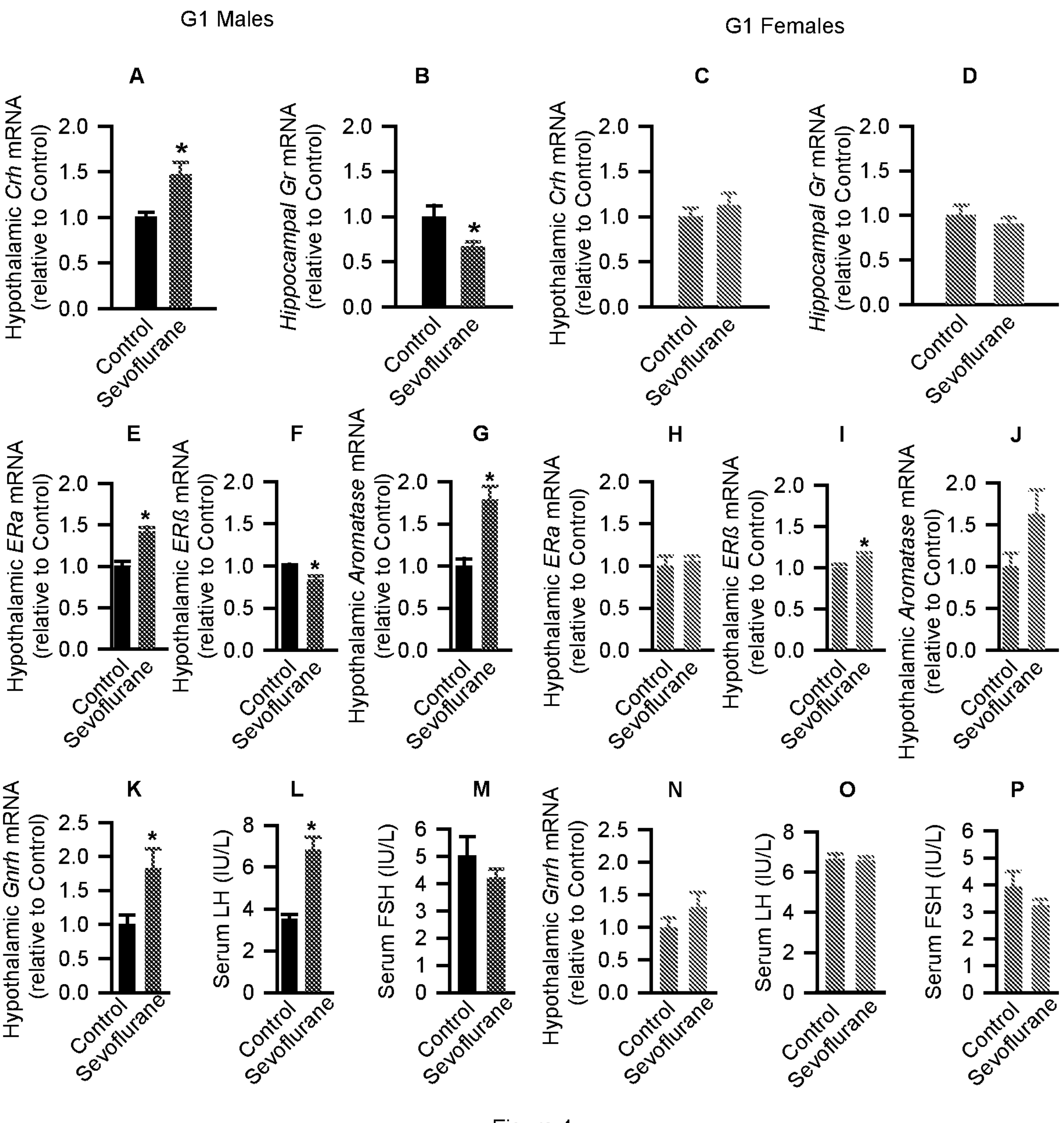
FIGS. 4A-4P are graphs illustrating that G1 male, but not female, rats, exposed to sevoflurane for 3 h on postnatal days (P) 56, 58 and 60 developed long-term alterations in the hypothalamic-pituitary-adrenal axis and hypothalamic-pituitary-gonadal axis at molecular level.

Long-term effects of repeated exposure of young adult rats to sevoflurane on the HPA and HPG axes at molecular level. Turning now to FIGS. 4N-4P, it can be seen that G1 male, but not female, rats, exposed to sevoflurane for 3 h on postnatal days (P) 56, 58 and 60 developed long-term alterations in the hypothalamic-pituitary-adrenal axis and hypothalamic-pituitary-gonadal axis at molecular level. FIGS. 4A-4D show the respective levels of hypothalamic Crh mRNA and hippocampal Gr mRNA in males (FIGS. 4A, 4B) and females (FIGS. 4C, 4D). Data normalized against control are means±SEM from 6 rats per treatment group (n=8, male Crh; n=5 in the Control group and n=4 in the Sevoflurane group in female Gr); *P<0.05 vs. Control.

FIGS. 4E-4J show levels of Era mRNA, Erβ mRNA and aromatase mRNA in the hypothalamus of male (FIGS. 4E-4G) and female (FIGS. 4H-4J) rats. Data normalized against control are means±SEM from 6 rats per treatment group; *P<0.05 vs. Control. In FIGS. 4K-P, shown are levels of hypothalamic Gnrh mRNA, serum levels of LH and FSH of male (FIGS. 4K-4M) and female (FIGS. 4N-4P) rats. Data are means±SEM from 8 rats per treatment group (n=6 per treatment group in FSH); *P<0.05 vs. Control.

In agreement with the exacerbated corticosterone responses to stress in sevoflurane-exposed G1 male rats, these same rats had increased hypothalamic Crh mRNA levels 2 hours after the restraint ($t_{(14)}$=−3.181; P=0.00667; FIG. 4A), as well as reduced levels of Gr mRNA in the hippocampus ($t_{(10)}$=2.493; P=0.0318; FIG. 4B). Neither hypothalamic Crh mRNA levels (FIG. 4C) nor hippocampal GrmRNA levels (FIG. 4D) were different in sevoflurane-exposed and control G1 female rats. The G1 male rats exposed to sevoflurane had increased and decreased hypothalamic levels of Era mRNA ($t_{(10)}$=−5.144; P=0.000435; FIG. 4E) and Erβ mRNA ($t_{(10)}$=3.156; P=0.0102; FIG. 4F), respectively. The hypothalamic levels of aromatase mRNA were also significantly increased in G1 sevoflurane-exposed males ($t_{(10)}$=−4.333; P=0.00148; FIG. 4G). In G1 females the hypothalamic levels of Erα mRNA (FIG. 4H) were not different between Sevoflurane and Control groups, while those of Erβ mRNA were slightly, though significantly increased in the Sevoflurane group ($t_{(10)}$=−2.521; P=0.0304; FIG. 4I) when compared to the Control group. The increase in the hypothalamic aromatase mRNA in sevoflurane-exposed G1 female rats did not achieve statistical significance ($t_{(10)}$=−1.878; P=0.0898; FIG. 4J).

Consistent with increased systemic levels of Tn in G1 sevoflurane-exposed male rats, these same rats had increased hypothalamic levels of Gnrh mRNA ($t_{(10)}$=−2.519; P=0.0304; FIG. 4K) and increased serum levels of LH ($t_{(14)}$=−4.932; P=0.000221; FIG. 4L), while serum levels of FSH ($t_{(10)}$=1.026; P=0.329; FIG. 4M) were not different from those in G1 control male rats. There were no significant treatment effects on the hypothalamic levels of Gnrh mRNA (FIG. 4N) or serum levels of LH (FIG. 4O) and FSH (FIG. 4P) in G1 female rats.

Figures 5A, 5B, 5C, 5D, 5E, 5F, 5G, 5H:
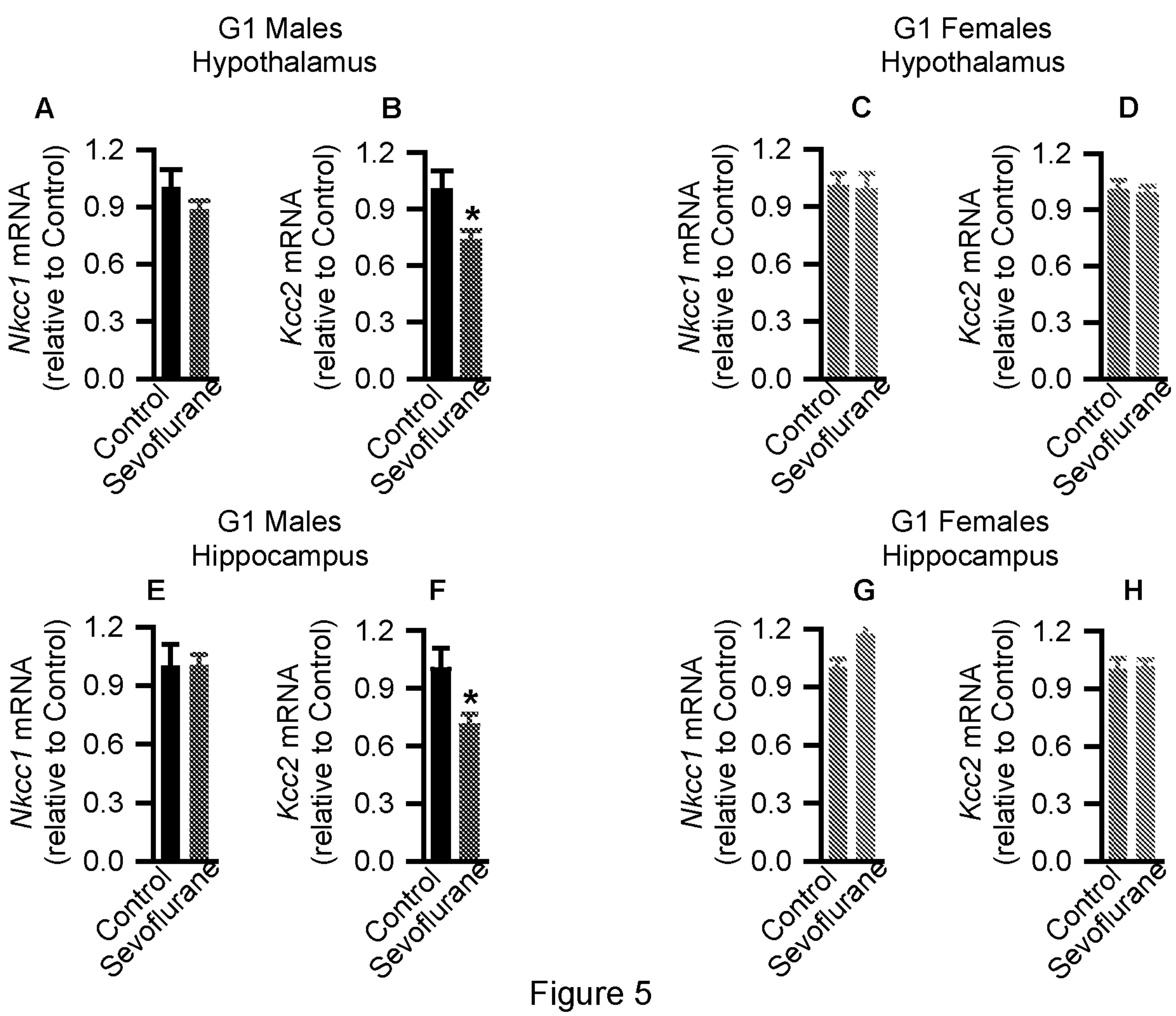
FIGS. 5A-5H are graphs illustrating that G1 male, but not female, rats, exposed to sevoflurane for 3 h on postnatal days (P) 56, 58 and 60 had decreased levels of hypothalamic and hippocampal Kcc2 mRNA, but unaltered levels of Nkcc1 mRNA.

Long-term effects of repeated exposure of young adult rats to sevoflurane on hypothalamic and hippocampal expression of Nkcc1 and Kcc2. Turning now to FIGS. 5A-5H, it can be seen that G1 male, but not female, rats, exposed to sevoflurane for 3 h on postnatal days (P) 56, 58 and 60 had decreased levels of hypothalamic and hippocampal Kcc2 mRNA, but unaltered levels of Nkcc1 mRNA. Shown in FIGS. 5A-5H are the respective levels of Nkcc1 mRNA and Kcc2 mRNA in the hypothalamus of G1 males (FIGS. 5A, 5B) and G1 females (FIGS. 5C, 5D) and in the hippocampus of G1 males (FIGS. 5E, 5F) and G1 females (FIGS. 5G, 5H). Data normalized against control are means±SEM from 6 rats per treatment group (n=5, female hippocampus in sevoflurane group); *P<0.05 vs. Controls. Color coding of experimental groups in FIGS. 5E-5H is applicable to all figures.

To assess whether exposure of young adult rats to sevoflurane led to persistent alterations in expression of $Cl^-$ transporters, brain hypothalamic and hippocampal tissue samples were collected more than 3 months after exposure. The G1 male rats from the Sevoflurane group had normal Nkcc1 mRNA levels ($t_{(10)}$=1.065; P=0.312; FIG. 5A), but decreased Kcc2 mRNA levels ($t_{(10)}$=2.273; P=0.0464; FIG. 5B) in the hypothalamus. In contrast, the G1 female rats from the Sevoflurane group had unaltered levels of both Nkcc1 mRNA ($t_{(10)}$=0.155; P=0.880; FIG. 5C) and Kcc2 mRNA ($t_{(10)}$=1.346; P=0.208; FIG. 5D) in the hypothalamus. In the hippocampus of G1 male rats from the Sevoflurane group, Kcc2 mRNA levels, but not Nkcc1 mRNA levels, were significantly reduced ($t_{(10)}$=2.387, P=0.0382, FIG. 5E, 5F). The hippocampal mRNA levels for Nkcc1 and Kcc2 were similar in control and sevoflurane-exposed G1 female rats (FIG. 5G,5H).

Figures 6A, 6N:
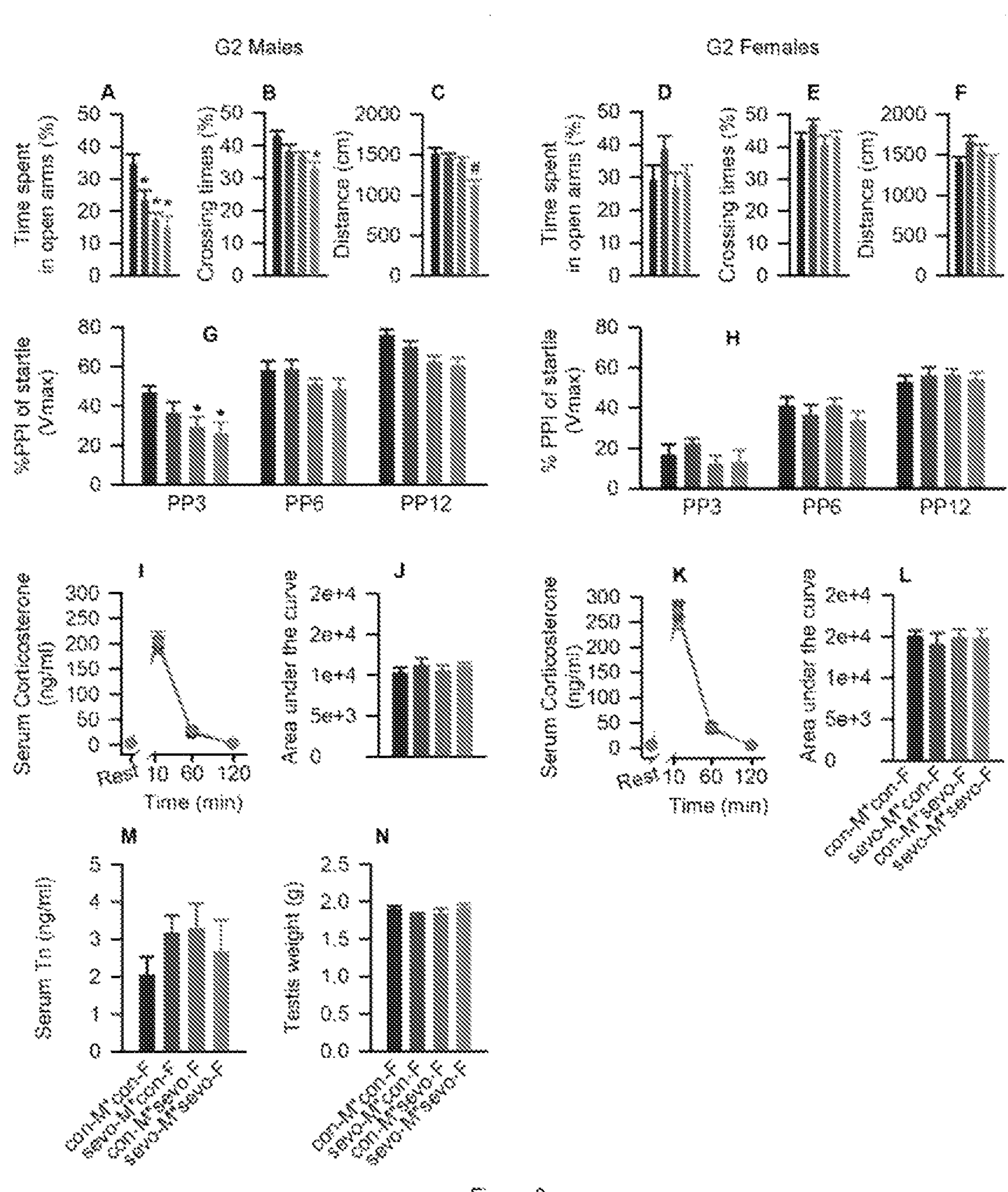
FIGS. 6A-6N are graphs illustrating that G2 male, but not female, offspring of exposed to sevoflurane for 3 h on postnatal days (P) 56, 58 and 60 rats, exhibited behavioral abnormalities, while G2 offspring had normal corticosterone responses to stress, serum levels of testosterone and testis weight.

Effects of repeated exposure of young adult rats to sevoflurane in their unexposed offspring. Turning now to FIGS. 6A-6N, it is shown that G2 male, but not female, offspring of exposed to sevoflurane for 3 h on postnatal days (P) 56, 58 and 60 rats, exhibited behavioral abnormalities, while G2 offspring had normal corticosterone responses to stress, serum levels of testosterone and testis weight. Shown in FIGS. 6A-6F are % of time spent in open arms of the EPM, number of crossing the open arms, and distance traveled by male (FIGS. 6A-6C) and female (FIGS. 6D-6F) rats. Data are means±SEM from ~16 rats per treatment group. FIGS. 6G, 6H shown % PPI responses at prepulse intensity of 3 dB, 6 dB and 12 dB in male (FIG. 6G) and female (FIG. 6H) rats. Data are means±SEM from ~16 rats per treatment group; *P<0.05 vs. con-M*con-F group. FIGS. 6I-6L are plots showing the respective levels of serum corticosterone across each collection point, as well as the total corticosterone responses (AUCg) in male (FIGS. 6I, 6J) and female (FIGS. 6K, 6L) rats. Serum levels of corticosterone at rest were taken as baselines for calculations of the total corticosterone responses. Data are means±SEM from 8 male rats per treatment group and from 8 female rats per treatment group. FIGS. 6M, 5N are histograms showing serum levels of testosterone (n=8 for each treatment group) and testis weight in G2 males (n=6 for each treatment group). Color coding of experimental groups in FIGS. 6M, 6N is applicable to all figures.

In G2 males, there was a significant between-subjects effect of parental exposure to sevoflurane on time spent in open arms ($F_{(3,58)}$=8.514, P<0.001; FIG. 6A) during the EPM test. Specifically, G2 male progeny of sevoflurane exposed fathers and unexposed mothers (P=0.040), unexposed fathers and exposed mothers (P<0.001), and exposed fathers and exposed mothers (P<0.001) spent less time in open arms when compared to G2 male offspring of control fathers and control mothers. Also, there were significant between-subjects effects of parental exposure to sevoflurane on number of crossings ($F_{(3,58)}$=4.657, P=0.006; FIG. 6B) and distance traveled ($F_{(3,58)}$=6.288, P<0.001; FIG. 6C) during the EPM test. Only G2 male offspring of both exposed parents made fewer crossings (P=0.003) and traveled shorter distances (P<0.001). All groups of G2 females were similar in respect to time spent in open arms (FIG. 6D), number of crossings (FIG. 6E) and distances traveled (FIG. 6F) during the EPM test.

There was a significant effect of parental sevoflurane exposure on PPI of startle responses in G2 male rats ($F_{(3,174)}$=7.590, P<0.001; FIG. 6G). Multiple pairwise comparisons indicated that when compared to offspring of unexposed parents only G2 males of both exposed parents (P=0.009) or those of control fathers and exposed mothers (P=0.027) exhibited reduced PPI of startle at PP3. In contrast to G2 males, there was no significant treatment effect on PPI of startle in G2 female rats ($F_{(3,168)}$=0.584, P=0.627; FIG. 6H). The startle amplitudes were similar among all experimental groups of G2 male ($F_{(3,58)}$=1.991, P=0.125) and G2 female ($F_{(3,56)}$=0.514, P=0.674) rats.

Measurements of serum levels of corticosterone in G2 male and female rats before and after physical restraint revealed no differences among all experimental groups within the same sex ($F_{(3,28)}$=0.335, P=0.80, males; FIGS. 6I, J, and $F_{(3,28)}$=0.142, P=0.934, females; FIG. 6K,L). There were no significant treatment effects of parental exposure to sevoflurane on serum levels of Tn ($F_{(3,20)}$=0.794, P=0.511, FIG. 6M) and testis weight ($F_{(3,20)}$=1.288, P=0.306, FIG. 6N) in G2 males.

Figures 7, 7A, 7B, 7C, 7D, 7E, 7F, 7G, 7H, 7I, 7J, 7K, 7L:
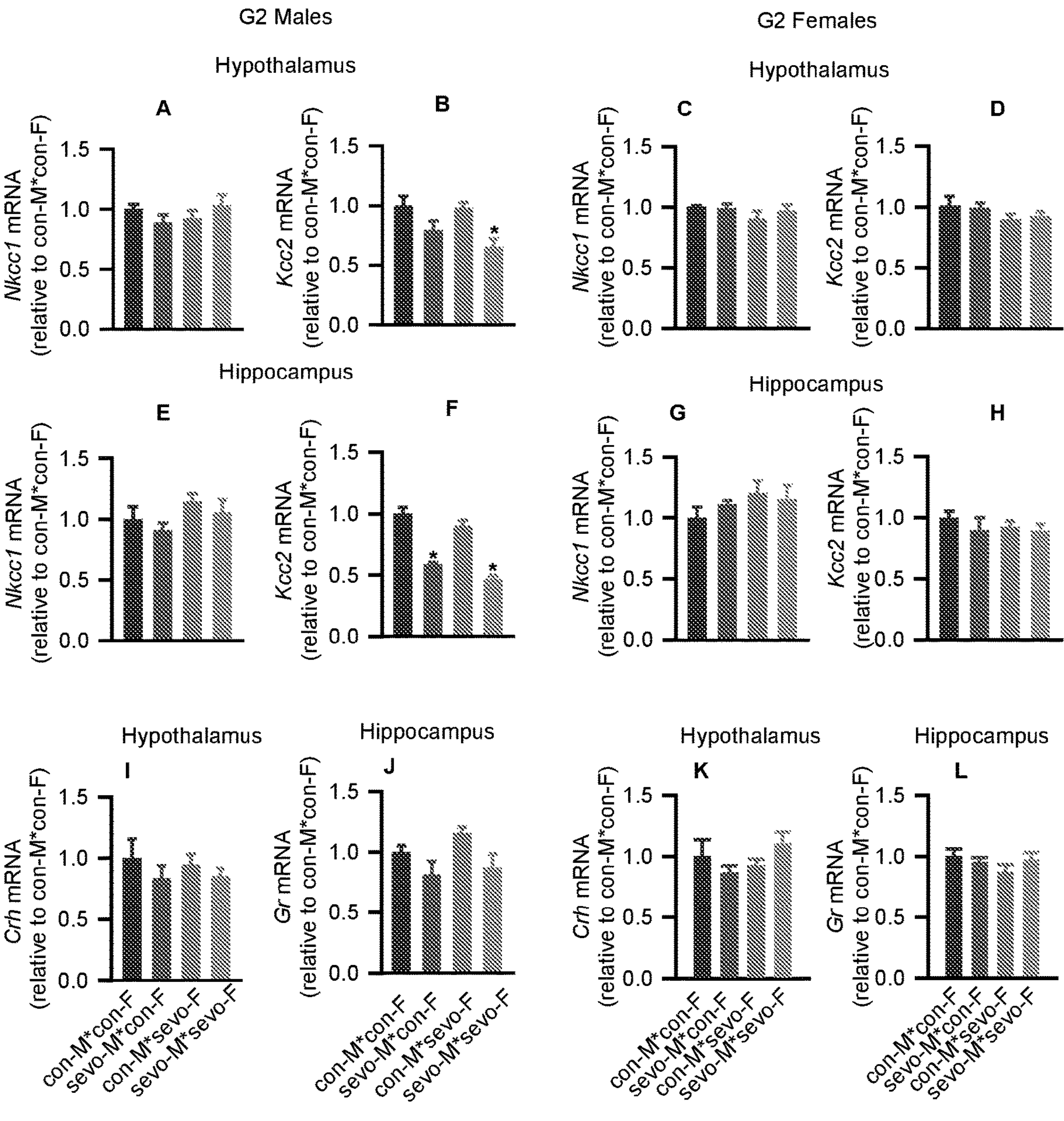
FIGS. 7A-7L are graphs illustrating that G2 male, but not female, offspring of exposed to sevoflurane for 3 h on postnatal days (P) 56, 58 and 60 rats, had decreased levels of hypothalamic and hippocampal Kcc2 mRNA, but unaltered levels hypothalamic Crh mRNA and hippocampal Gr mRNA.

Effects of repeated exposure of young adult rats to sevoflurane on expression of Nkcc1, Kcc2, Crh and Grs in the hypothalamus and hippocampus of their unexposed offspring. Turning now to FIGS. 7A-7L, G2 male, but not female, offspring of exposed to sevoflurane for 3 h on postnatal days (P) 56, 58 and 60 rats, had decreased levels of hypothalamic and hippocampal Kcc2 mRNA, but unaltered levels hypothalamic Crh mRNA and hippocampal Gr mRNA. Shown in FIGS. 7A-7H are the respective levels of Nkcc1 mRNA and Kcc2 mRNA in the hypothalamus of G2 males (FIGS. 7A, 7B) and G2 females (FIGS. 7C, 7D) and in the hippocampus of G2 males (FIG. 7E, FIG. 7F) and G1 females (FIGS. 7G, 7H). Data normalized against control are means±SEM from 6 rats per treatment group (n=5, female hypothalamic Nkcc1 in con-M*con-F group); *P<0.05 vs. con-M*con-F. FIGS. 7I-7L are plots showing the levels of Crh mRNA in the hypothalamus and GrmRNA in the hippocampus in G2 males (FIGS. 7I, 7J) and G2 females (FIGS. 7K, 7L). Color coding of experimental groups in FIGS. 7I-7L is applicable to all figures.

There were similar levels of Nkcc1 mRNA in the hypothalamus of all four treatment groups of G2 male rats ($F_{(3,20)}$=0.928, P=0.446, FIG. 7A), but there was a significant between-subjects effect of parental sevoflurane exposure on hypothalamic Kcc2 mRNA levels ($F_{(3,20)}$=5.636, P=0.006, FIG. 7B). Specifically, G2 male progeny of sevoflurane exposed fathers and mothers had lower levels of Kcc2 mRNA when compared to G2 male offspring of control fathers and control mothers (P=0.012). In the hypothalamus of G2 females there were not significant between-subjects effects of parental sevoflurane exposures on the Nkcc1 mRNA levels ($F_{(3,19)}$=0.886, P=0.466, FIG. 7C) and Kcc2 mRNA levels ($F_{(3,20)}$=0.738, P=0.629, FIG. 7D).

In the hippocampus of G2 males there were no significant effects of parental sevoflurane exposure on Nkcc1 mRNA levels ($F_{(3,20)}$=1.357, P=0.284, FIG. 7E), but there was a significant effect on Kcc2 mRNA levels ($F_{(3,20)}$=41.375, P<0.001, FIG. 7F). Only male offspring of both exposed parents (P<0.001) and offspring of exposed fathers and control mothers (P<0.001) had reduced hippocampal Kcc2 mRNA levels. In the hippocampus of G2 females there were not significant between-subjects effects of parental neonatal sevoflurane exposures on the Nkcc1 mRNA level ($F_{(3,20)}$=0.925, P=0.447, FIG. 7G) and Kcc2 mRNA level ($F_{(3,20)}$=0.524, P=0.671, FIG. 7H).

Levels of Crh mRNA in the hypothalamus ($F_{(3,20)}$=0.519, P=0.674, FIG. 7I) and Gr mRNA levels in the hippocampus ($F_{(3,19)}$=3.293, P=0.043, FIG. 7J) of G2 males were not different between all four treatment groups. In addition, there were no significant between-subjects effects of parental sevoflurane exposure on hypothalamic Crh mRNA ($F_{(3,20)}$=1.225, P=0.327, FIG. 7K) or hippocampal Gr mRNA levels ($F_{(3,19)}$=0.860, P=0.479, FIG. 7L) in G2 female rats.

Figures 8, 8A, 8B, 8C, 8D:
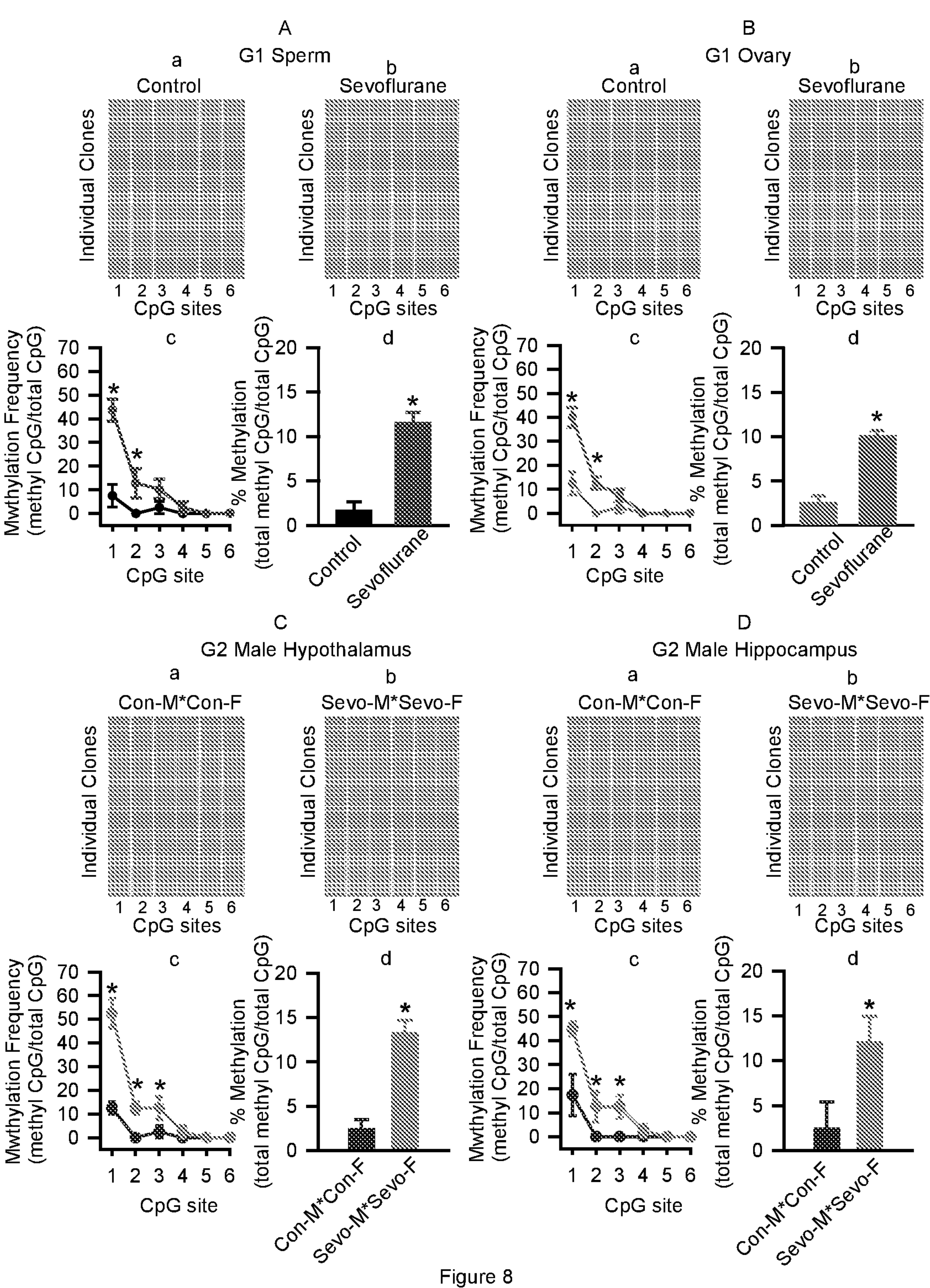
FIGS. 8A-8D are graphs illustrating DNA methylation in the promotor region of Kcc2 gene in G1 sperm and ovary and G2 hypothalamus and hippocampus.
Figure 9:
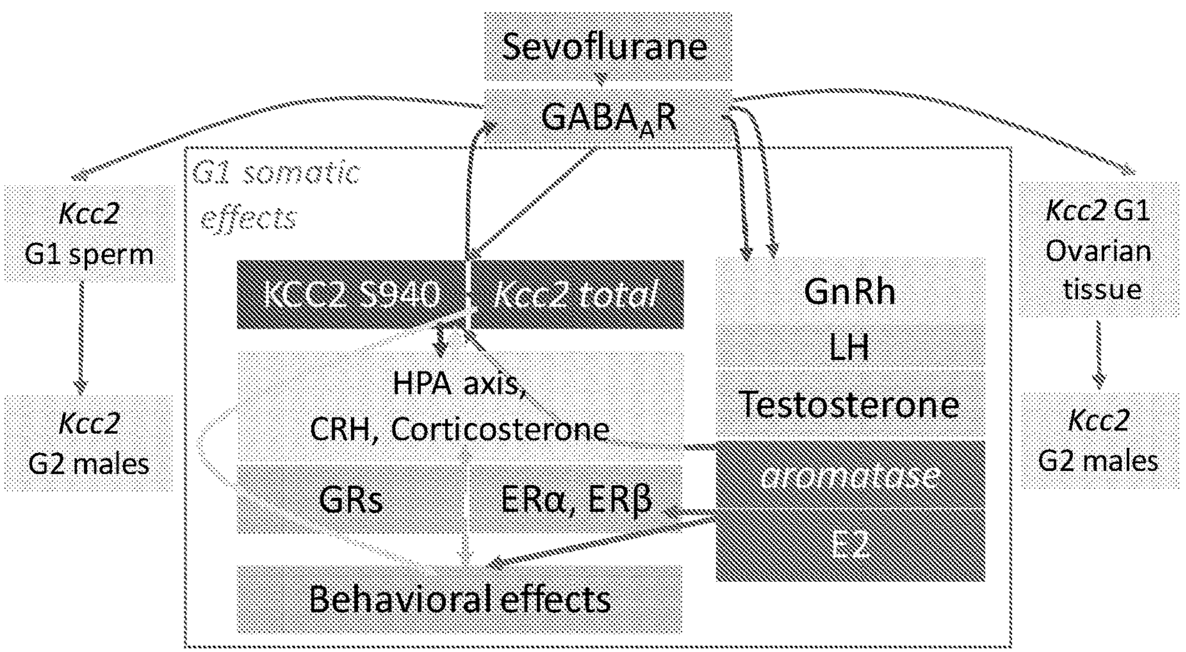
FIG. 9 provides hypothetical pathways mediating intergenerational effects of sevoflurane in young adulthood.
Figure 10:
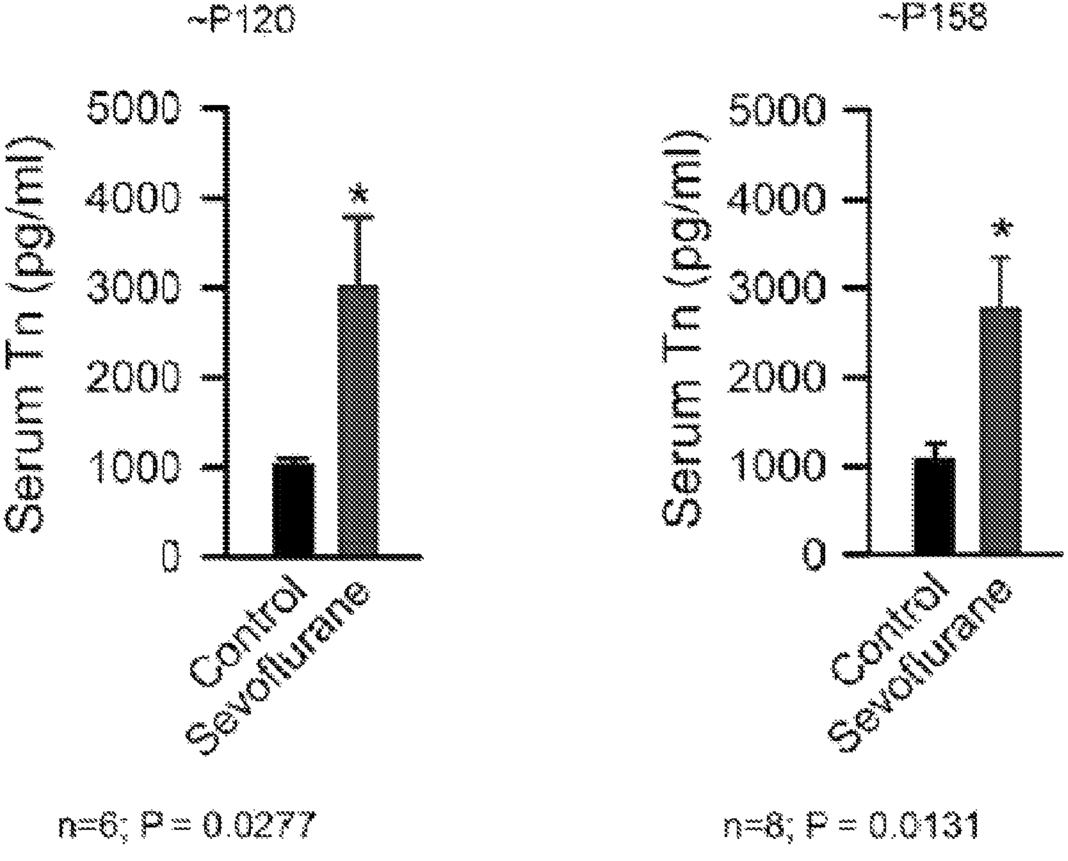
FIG. 10 provides graphs illustrating that adult anesthesia with sevoflurane induces long-lasting increases in serum levels of testosterone (Tn).

Effects of repeated exposure of young adult rats to sevoflurane on DNA methylation of the Kcc2 gene in sperm and ovary of G1 exposed rats and in the hypothalamus and hippocampus of their G2 offspring. Turning now to FIGS. 8A-8D, shown is DNA methylation in the promotor region of Kcc2 gene in G1 sperm and ovary and G2 hypothalamus and hippocampus. (FIG. 8A,a-d) Bisulfite sequencing of CpG sites in the Kcc2 gene of 10 clones from four individual sperm DNA samples isolated from control and sevoflurane-exposed G1 male rats. Heat maps show distribution of unmethylated (blue cells) and methylated (red cells) CpG sites in sperm DNA samples isolated from control (FIG. 8A,a) and sevoflurane-exposed (FIG. 8A,b) G1 male rats. Histograms showing methylation frequency at each CpG site (FIG. 8A,c) and DNA methylation level at all 6 CpG sites (FIG. 8A,d). The results of similar analysis of bisulfite sequencing of CpG di-nucleotides in the Kcc2 gene of 10 clones from four individual ovary DNA samples isolated from sevoflurane-exposed and control G1 female rats shown in (FIG. 8B,a-d). Shown in FIGS. 8C and 8D are the respective methylation frequency at each CpG site and DNA methylation level at all 6 CpG sites in the Kcc2 gene of 10 clones in the hypothalamus (FIG. 8C,a-d) and hippocampus (FIG. 8D,a-d) of G2 male offspring of control sires and control dams and of sevoflurane-exposed sires and dams. Data are means±SEM from 4 rats per treatment group; *P<0.05 vs. Control (FIG. 8A, 8B) and vs. Con-M*Con-F (FIG. 8C, 8D).

There was a significant effect of treatment ($F_{(1,36)}$=30.8, P<0.001) and within-subjects effect of CpG site ($F_{(5,36)}$=20.066, P<0.001) on the frequency of methylation of CpG sites in the Kcc2 gene promoter in sperm of G1 rats (FIGS. 8A-8D). There was a statistically significant interaction between CpG site and treatment ($F_{(5,36)}$=10.036, P<0.001). Pairwise multiple comparison analysis found that young adult exposure to sevoflurane led to increased methylation in G1 male rats at CpG site 1 (P<0.001 vs control), and CpG site 2 (P=0.006 vs control). Similarly, there was a significant effect of treatment ($F_{(1,36)}$=34.714, P<0.001) and within-subjects effect of CpG site ($F_{(5,36)}$=42.686, P<0.001) on the frequency of CpG site methylation in the Kcc2 gene promoter in ovarian tissue of G1 rats (FIG. 8B). There was a statistically significant interaction between CpG site and treatment ($F_{(5,36)}$=12.343, P<0.001). Pairwise multiple comparison analysis found that young adult exposure to sevoflurane lead to increased methylation in G1 female rats at CpG site 1 (P<0.001 vs control), and CpG site 2 (P<0.001 vs control).

There was a significant between-subjects effect of parental treatment on CpG site methylation in the promoter of Kcc2 gene in the hypothalamus of male offspring of both exposed parents ($F_{(1,36)}$=48.286, P<0.001), and within-subject effect of CpG site ($F_{(5,36)}$=42.629, P<0.001) (FIG. 8C). There was also a statistically significant interaction between CpG site and treatment ($F_{(5,36)}$=15.886, P<0.001). Pairwise multiple comparison analyses showed that young adult parental exposure to sevoflurane led to increased DNA methylation in the Kcc2 gene promoter in the hypothalamus of G2 male progeny of both exposed parents at CpG site 1 (P<0.001 vs G2 males from the con-M*con-F group), and CpG site 2 (P=0.002 vs G2 males from the con-M*con-F group) and CpG site 3 (P=0.013 vs G2 males from the con-M*con-F group). There was a significant between-subjects effect of parental treatment on CpG site methylation in the promoter of Kcc2 gene in the hippocampus of male offspring of both exposed parents ($F_{(1,36)}$=21.740, P<0.001, and within subject effect of CpG site ($F_{(5,36)}$=20.852, P<0.001) (FIG. 8D). There was also a statistically significant interaction between CpG site and treatment ($F_{(5,36)}$=5.268, P<0.001). Pairwise multiple comparison analyses found that young adult parental exposure to sevoflurane led to increased DNA methylation in the Kcc2 gene promoter in the hippocampus of G2 male progeny of both exposed parents at CpG site 1 (P<0.001 vs con-M*con-F), CpG site 2 (P=0.018 vs con-M*con-F) and CpG site 3 (P=0.018 vs con-M*con-F).

Figures 11A, 11B, 11C, 11D:
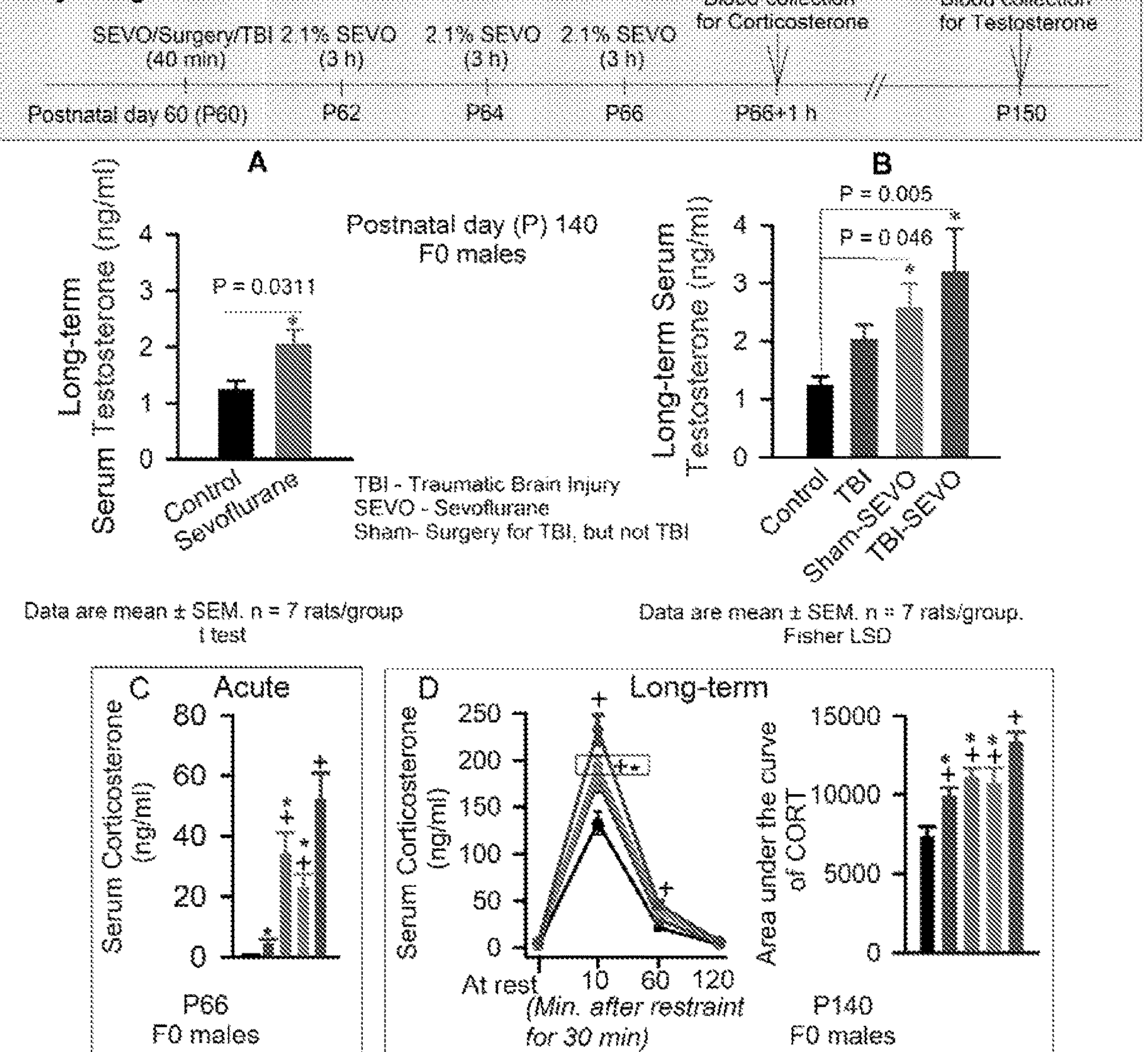
FIGS. 11A-11D show that exposure of young adult rats to sevoflurane (SEVO) results in long-term increase in serum levels of testosterone (FIG. 11A).

Exposure of young adult rats to sevoflurane (SEVO) results in long-term increase in serum levels of testosterone. The Sprague-Dawley F0 male rats in the TBI group had SEVO exposure for 40 min to conduct a craniectomy and injury hub implantation on P60. After 60 min of recovery, they were reanesthetized with SEVO for 3 min to induce moderate TBI using a midline fluid percussion injury (FPI) model. The TBI+SEVO group had additional exposure to SEVO for 3 h on P62, P64, and P66. These subsequent exposures to SEVO, which may be needed to treat accompanying conditions, such as orthopedic, abdominal, or thoracic injuries, were used to study whether the effects of SEVO, surgery, and TBI interact to induce their effects. The Sham group had all exposures to SEVO and craniectomy but not TBI. The SEVO-SEVO group had all exposures to SEVO only. The control group had none of these procedures, except being placed in a new cage for an equivalent duration and number of times. A subset of F0 male rats was sacrificed on P66 1 h after the last exposure to SEVO for 3 h or at equivalent timepoints to collect blood to study acute neuroendocrine effects (FIG. 11A). The serum corticosterone levels before and after physical restraint for 30 min were measured ion P140. Ten days after completing the in vivo studies, the same rats were sacrificed and trunk blood samples were collected to measure serum levels of testosterone.

FIGS. 11A-11D show that exposure of young adult rats to sevoflurane (SEVO) results in long-term increase in serum levels of testosterone (FIG. 11A). FIG. 11B shows that effects of SEVO and surgery (to induce traumatic brain injury, TBI) and TBI interact to induce even greater increases in testosterone levels. FIGS. 11C-11D shows that the combined effects of SEVO, surgery and TBI to induce increases in testosterone levels may not be explained by just their cummulative stress-like effects.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

References cited herein are as follows below. Reference citations are indicated in standard fashion (indicated as one or more superscripted numbers at the end of a sentence, such that the numbers correspond to the reference number as given herein below).

1. Weiser T G, Haynes A B, Molina G, Lipsitz S R, Esquivel M M, Uribe-Leitz T, Fu R, Azad T, Chao T E, Berry W R, Gawande A A: Size and distribution of the global volume of surgery in 2012. *Bull World Health Organ* 2016; 94:201-9F.
2. Brown E N, Lydic R, Schiff N D: General anesthesia, sleep, and coma. *N Engl J Med* 2010; 363:2638-50.
3. Vutskits L, Xie Z: Lasting impact of general anaesthesia on the brain: mechanisms and relevance. *Nat Rev Neurosci* 2016; 17:705-17.
4. Monk T G, Weldon B C, Garvan C W, Dede D E, van der Aa M T, Heilman K M, Gravenstein J S: Predictors of cognitive dysfunction after major noncardiac surgery. *Anesthesiology* 2008; 108:18-30.
5. Ju L S, Yang J J, Morey T E, Gravenstein N, Seubert C N, Resnick J L, Zhang J Q, Martynyuk A E: Role of epigenetic mechanisms in transmitting the effects of neonatal sevoflurane exposure to the next generation of male, but not female, rats. *Br J Anaesth* 2018; 121: 406-16.
6. Tan S, Xu C, Zhu W, Willis J, Seubert C N, Gravenstein N, Sumners C, Martynyuk A E: Endocrine and neurobehavioral abnormalities induced by propofol administered to neonatal rats. *Anesthesiology* 2014; 121:1010-1117.
7. Xu C, Tan S, Zhang J, Seubert C N, Gravenstein N, Sumners C, Vasilopoulos T, Martynyuk A E: Anesthesia with sevoflurane in neonatal rats: Developmental neuroendocrine abnormalities and alleviating effects of the corticosteroid and Cl(−) importer antagonists. *Psychoneuroendocrinology* 2015; 60: 173-81.
8. Ben-Ari Y: The GABA excitatory/inhibitory developmental sequence: a personal journey. *Neuroscience* 2014; 279:187-219.
9. Khazipov R, Valeeva G, Khalilov I: Depolarizing GABA and developmental epilepsies. *CNS Neurosci Ther* 2015; 21:83-91.
10. Lemonnier E, Villeneuve N, Sonie S, Serret S, Rosier A, Roue M, Brosset P, Viellard M, Bernoux D, Rondeau S, Thummler S, Ravel D, Ben-Ari Y: Effects of bumetanide on neurobehavioral function in children and adolescents with autism spectrum disorders. *Transl Psychiatry* 2017; 7:e1056.
11. Tang X, Kim J, Zhou L, Wengert E, Zhang L, Wu Z, Carromeu C, Muotri A R, Marchetto M C, Gage F H, Chen G: KCC2 rescues functional deficits in human neurons derived from patients with Rett syndrome. *Proc Natl Acad Sci USA* 2016; 113:751-6.
12. Luscher B, Fuchs T: GABAergic control of depression-related brain states. *Adv Pharmacol* 2015; 73:97-144.
13. Ju L S, Yang J J, Gravenstein N, Seubert C N, Morey T E, Sumners C, Vasilopoulos T, Yang J J, Martynyuk A E: Role of environmental stressors in determining the developmental outcome of neonatal anesthesia. *Psychoneuroendocrinology* 2017; 81:96-104.
14. Lee B H, Chan J T, Kraeva E, Peterson K, Sall J W: Isoflurane exposure in newborn rats induces long-term cognitive dysfunction in males but not females. *Neuropharmacology* 2014; 83:9-17.
15. Hewitt S A, Wamsteeker J I, Kurz E U, Bains J S: Altered chloride homeostasis removes synaptic inhibitory constraint of the stress axis. *Nat Neurosci* 2009; 12:438-43.
16. Sarkar J, Wakefield S, MacKenzie G, Moss S J, Maguire J: Neurosteroidogenesis is required for the physiological response to stress: role of neurosteroid-sensitive GABAA receptors. *J Neurosci* 2011; 31:18198-210.
17. Ostroumov A, Thomas A M, Kimmey B A, Karsch J S, Doyon W M, Dani J A: Stress increases ethanol self-administration via a shift toward excitatory GABA signaling in the ventral tegmental area. *Neuron* 2016; 92:493-504.
18. Tsukahara T, Masuhara M, Iwai H, Sonomura T, Sato T: The effect of repeated stress on KCC2 and NKCC1 immunoreactivity in the hippocampus of female mice. *Data Brief* 2016; 6:521-5.
19. Quennell J H, Howell C S, Roa J, Augustine R A, Grattan D R, Anderson G M: Leptin deficiency and diet-induced obesity reduce hypothalamic kisspeptin expression in mice. *Endocrinology* 2001; 152:1541-50.

20. Weinstock M, Razin M, Schorer-Apelbaum D, Men D, McCarty R: Gender differences in sympathoadrenal activity in rats at rest and in response to footshock stress. *Int J Dev Neurosci* 1998; 16:289-95.

21. Figueiredo H F, Ulrich-Lai Y M, Choi D C, Herman J P: Estrogen potentiates adrenocortical responses to stress in female rats. *Am J Physiol Endocrinol Metab* 2007; 292: E1173-82.

22. Iwasaki-Sekino A, Mano-Otagiri A, Ohata H, Yamauchi N, Shibasaki T: Gender differences in corticotropin and corticosterone secretion and corticotropin-releasing factor mRNA expression in the paraventricular nucleus of the hypothalamus and the central nucleus of the amygdala in response to footshock stress or psychological stress in rats. *Psychoneuroendocrinology* 2009; 34:226-37.

23. Camille Melon L, Maguire J: GABAergic regulation of the HPA and HPG axes and the impact of stress on reproductive function. *J Steroid Biochem Mol Biol* 2016; 160:196-203.

24. DeFazio R A, Heger S, Ojeda S R, Moenter S M: Activation of A-type gamma-aminobutyric acid receptors excites gonadotropin-releasing hormone neurons. *Mol Endocrinol* 2002; 16:2872-91.

25. Herbison A E, Moenter S M: Depolarising and hyperpolarising actions of GABA(A) receptor activation on gonadotrophin-releasing hormone neurones: towards an emerging consensus. *J Neuroendocrinol* 2011; 23:557-69.

26. Weiser M J, Handa R J: Estrogen impairs glucocorticoid dependent negative feedback on the hypothalamic-pituitary-adrenal axis via estrogen receptor alpha within the hypothalamus. *Neuroscience* 2009; 159:883-95.

27. Weiser M J, Foradori C D, Handa R J: Estrogen receptor beta activation prevents glucocorticoid receptor-dependent effects of the central nucleus of the amygdala on behavior and neuroendocrine function. *Brain Res* 2010; 1336:78-88.

28. Handa R J, Nunley K M, Lorens S A, Louie J P, McGivern R F, Bollnow M R: Androgen regulation of adrenocorticotropin and corticosterone secretion in the male rat following novelty and foot shock stressors. *Physiol Behav* 1994; 55:117-24.

29. Rodgers A B, Morgan C P, Bronson S L, Revello S, Bale T L: Paternal stress exposure alters sperm microRNA content and reprograms offspring HPA stress axis regulation. *J Neurosci* 2013; 33: 9003-12.

30. Tang C K, Chalon J, Markham J P, Ramanathan S, Turndorf H: Exposure of sires to enflurane affects learning function of murine progeny. *Anesth Analg* 1984; 63: 729-30.

What is claimed is:

1. A method of treating a subject having a clinical condition associated with low circulating levels of testosterone, comprising:

administering to the subject a therapeutically effective dose of sevoflurane, wherein the subject is not undergoing a surgical procedure or does not require a surgical procedure, and the therapeutically effective dose of sevoflurane is from 0.05 vol % to 2 vol %, thereby treating the clinical condition associated with low circulating levels of testosterone.

2. The method of claim 1, wherein the administering is via inhalation.

3. The method of claim 2, wherein the inhalation is via administration a vaporizer.

4. The method of claim 1, wherein the administering is nasally.

5. The method of claim 1, wherein the therapeutically effective dose increases serum levels of testosterone in the subject from 1 day to 150 days after the administration of the therapeutically effective dose of sevoflurane.

6. The method of claim 1, wherein the therapeutically effective dose increases serum levels of testosterone by about 10% to about 350% within about 12 hours to about 96 hours following administration.

7. The method of claim 1, wherein the therapeutically effective dose increases serum levels of testosterone to about 270 ng/dL to about 1070 ng/dl within about 12 hours to about 96 hours following administration.

8. The method of claim 1, wherein the administering comprises daily administration for about one day to about 10 days.

9. The method of claim 1, wherein the therapeutically effective dose is about 0.05 vol % to about 3 vol % when administered via inhalation.

10. The method of claim 9, wherein the therapeutically effective dose is about 0.05 vol % to about 2 vol % when administered via inhalation.

11. The method of claim 9, wherein the therapeutically effective dose is about 0.05 vol % to about 1 vol % when administered via inhalation.

12. The method of claim 1, wherein the sevoflurane is administered via inhalation in oxygen.

13. The method of claim 1, wherein the sevoflurane is administered via inhalation in a gas comprising about 50 vol % to about 80 vol % $N_2O$ and about 25 vol % to about 50 vol % $O_2$.

14. The method of claim 1, wherein the clinical condition associated with low circulating levels of testosterone is Klinefelter's Syndrome, Noonan Syndrome, testicular injury, or congenital anorchidism.

15. The method of claim 1, wherein the clinical condition associated with low circulating levels of testosterone is prolactinoma, presence of a pituitary tumor, Prader-Willi syndrome, or Kallmann's syndrome.

16. The method of claim 1, wherein the clinical condition associated with low circulating levels of testosterone is late-onset hypogonadism.

17. The method of claim 1, wherein sevoflurane is administered to the subject daily for at least two days.

18. A method of treating a subject having a clinical condition associated with low circulating levels of testosterone, comprising:

administering to the subject a therapeutically effective dose of sevoflurane, wherein sevoflurane is administered to the subject daily for at least two days, thereby treating the clinical condition associated with low circulating levels of testosterone.

19. The method of claim 18, wherein the therapeutically effective dose of sevoflurane is from 0.05 vol % to 2 vol %.

* * * * *